US008119041B2

(12) United States Patent
Akiba et al.

(10) Patent No.: US 8,119,041 B2
(45) Date of Patent: *Feb. 21, 2012

(54) NON-RESONANT TWO-PHOTON ABSORPTION INDUCTION METHOD AND PROCESS FOR EMITTING LIGHT THEREBY

(75) Inventors: Masaharu Akiba, Kanagawa (JP); Jun Kawamata, Hokkaido (JP)

(73) Assignee: Fujifilm Corporation, Tokyo (JP)

(*) Notice: Subject to any disclaimer, the term of this patent is extended or adjusted under 35 U.S.C. 154(b) by 272 days.

This patent is subject to a terminal disclaimer.

(21) Appl. No.: 10/233,424

(22) Filed: Sep. 4, 2002

(65) Prior Publication Data

US 2003/0162124 A1    Aug. 28, 2003

(30) Foreign Application Priority Data

Sep. 5, 2001 (JP) .............................. P.2001-268989
Sep. 5, 2001 (JP) .............................. P.2001-268990
Sep. 5, 2001 (JP) .............................. P.2001-268991

(51) Int. Cl.
G02F 1/361 (2006.01)
G03F 7/04 (2006.01)
G03F 7/031 (2006.01)
C09K 11/06 (2006.01)
C07C 49/11 (2006.01)
G03C 1/12 (2006.01)
G11B 7/244 (2006.01)
G11B 7/245 (2006.01)
G11B 7/247 (2006.01)

(52) U.S. Cl. ................. 252/582; 252/587; 252/301.16; 522/2; 8/569; 430/281.1; 546/95; 546/96; 564/305; 564/308; 568/308; 568/379

(58) Field of Classification Search .................. 252/582, 252/587, 301.16; 522/2; 372/53; 8/659; 430/281.1; 427/510; 546/95, 96; 564/305, 564/308; 568/308, 379
See application file for complete search history.

(56) References Cited

U.S. PATENT DOCUMENTS

| | | | |
|---|---|---|---|
| 2,860,984 A | | 11/1958 | Jones |
| 3,652,275 A | * | 3/1972 | Baum et al. |
| 3,715,351 A | | 2/1973 | Brooker et al. |
| 4,079,183 A | * | 3/1978 | Green |
| 4,080,496 A | | 3/1978 | Mee |
| 4,259,432 A | | 3/1981 | Kondoh et al. |
| 4,415,621 A | | 11/1983 | Specht et al. |
| 4,535,052 A | * | 8/1985 | Anderson et al. ........... 430/277.1 |
| 4,824,765 A | * | 4/1989 | Sperry et al. .................. 430/281 |
| 4,921,827 A | * | 5/1990 | Ali et al. .................. 430/281 X |
| 4,987,056 A | * | 1/1991 | Imahashi et al. ........... 430/281.1 |
| 5,079,128 A | | 1/1992 | Katagiri |
| 5,268,862 A | | 12/1993 | Rentzepis ..................... 365/151 |
| 5,422,204 A | | 6/1995 | Yoshinaga et al. |
| 5,667,943 A | * | 9/1997 | Boggs et al. .................. 430/343 |
| 5,770,737 A | | 6/1998 | Reinhardt et al. ............ 546/285 |
| 6,153,660 A | * | 11/2000 | Fujimaki et al. ................ 522/29 |
| 6,187,502 B1 | | 2/2001 | Chapman et al. |
| 6,316,153 B1 | * | 11/2001 | Goodman et al. ................ 430/8 |
| 6,335,144 B1 | * | 1/2002 | Murota et al. ............. 430/281.1 |
| 6,406,647 B1 | * | 6/2002 | Thakur ......................... 252/582 |
| 6,852,766 B1 | | 2/2005 | DeVoe |
| 7,531,667 B2 | * | 5/2009 | Takizawa ...................... 548/219 |
| 7,582,390 B2 | * | 9/2009 | Takizawa ......................... 430/1 |
| 7,582,391 B2 | * | 9/2009 | Takizawa ......................... 430/1 |
| 2001/0003032 A1 | | 6/2001 | Harada et al. |

FOREIGN PATENT DOCUMENTS

| | | | |
|---|---|---|---|
| EP | 0 942 431 A2 | * | 9/1999 |
| JP | 55-50001 A | | 4/1980 |
| JP | 56-135557 A | | 10/1981 |
| JP | 59-28325 B2 | | 7/1984 |
| JP | 62-165747 A | | 7/1987 |
| JP | 1-229694 A | | 9/1989 |
| JP | 03089219 A | * | 4/1991 |
| JP | 5-257279 A | | 10/1993 |
| JP | 08-29995 | * | 2/1996 |
| JP | 2001-166467 A | | 6/2001 |
| WO | WO 97/09043 | | 3/1997 |
| WO | WO 99/53242 | | 10/1999 |

OTHER PUBLICATIONS

Machine translation and Patent Abstract of Japan, JPO, Pub No. 08-299995, Mitsubishi Chem Corp, (Japan Patent Office, Nov. 14, 2005), pp. 1-16, http://www19.ipdl.ncipi.go.jp/PA1/cgi-bin/PA1DETAIL.*
Feldner et al, "Nonlinear Optical Properties of Specific Polymethines: Influence of Substituents and Chain Length", Nonlinear Optics, 2000, vol. 26, pp. 99-106, (2000-month unavailable).*
Brian H. Cumpston et al., "Two-photon polymerization initiators for threedimensional optical data storage and microfabrication", Nature |vol. 398 | Mar. 4, 1999 | obtained online @ www.nature.com (® 1999 Macmillan Magazines Ltd) pp. 51-54.*
Kevin D. Belfield, Katherine J. Schafer, Yong Liu, Jun Liu, Xiaobin Ren, Eric W. Van Stryland, "Multiphoton-absorbing organic materials for microfabrication, emerging optical applications and non-destructive three-dimensional imaging", Journal of Physical Organic Chemistry, vol. 13, Issue 12, Date: Dec. 2000, pp. 837-849.*
JPO on EAST, Patent Abstracts of Japan, Japan patent Office, Tokyo, Japan, JP 03089219 A (Apr. 1991), Abstract.*

(Continued)

Primary Examiner — Daniel S Metzmaier
(74) Attorney, Agent, or Firm — Sughrue Mion, PLLC

(57) ABSTRACT

The present invention provides a two-photon light-emitting compound represented by formula (1), an optical data recording medium comprising a compound represented by formula (1), a two-photon polymerizable composition comprising a polymerizable monomer or polymerizable oligomer and at least compound represented by formula (1), and a photopolymerization process:

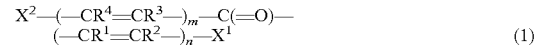

$$X^2\text{—}(\text{—}CR^4\text{=}CR^3\text{—})_m\text{—}C(\text{=}O)\text{—}$$
$$(\text{—}CR^1\text{=}CR^2\text{—})_n\text{—}X^1 \quad (1)$$

wherein $X^1$ and $X^2$ may be the same or different and each represent a substituted or unsubstituted aryl group or a substituted or unsubstituted heterocyclic group; $R^1$, $R^2$, $R^3$ and $R^4$ each independently represent a hydrogen atom or substituent; some of $R^1$, $R^2$, $R^3$ and $R^4$ may be connected to each other to form at least one ring; and n and m each independently represent an integer of from 1 to 4, with the proviso that when n and m are 2 or more, the plurality of $R^1$'s, $R^2$'s, $R^3$'s, and $R^4$'s each may be the same or different.

8 Claims, No Drawings

OTHER PUBLICATIONS

Guang S. HE et al., Two-Photon Pumped Cavity Lasing in Novel Dye Doped Bulk Matrix Rods, Appln. Phys. Lett. 1995, 67, 3703.

Bruce A. Reinhardt et al., Highly Active Two-Photon Dyes: Design, Synthesis, and Characterization Toward Application, Chem. Matter. 1998, 10,1863.

Marius Albota et al., Design of Organic Molecules with Large Two Photon Absorption Cross Sections, Science 1998, 281, 1653.

S. Kawata et al., Finer Features for Functional Microdevices, Nature, 2001, 412, 697 (regarding Two Photon polymerization).

S. Kawata et al., Three-Dimensional Optical Data Storage Using Photochromic Materials, Chem. Rev. 2000. 100. 1777 (regarding Two Photon Recording).

Japanese Office Action dated Feb. 27, 2008.

* cited by examiner

NON-RESONANT TWO-PHOTON ABSORPTION INDUCTION METHOD AND PROCESS FOR EMITTING LIGHT THEREBY

FIELD OF THE INVENTION

The present invention relates to a material which exerts a non-linear optical effect and more particularly to an organic non-linear optical material having a large non-resonant two-photon absorption cross-section and a large efficiency of light emission from excited state developed by non-resonant two-photon absorption.

The present invention further relates to an organic non-linear optical material having a great non-resonant two-photon absorption induced light emitting efficiency.

The present invention also relates to an optical data recording medium capable of recording data with laser beam and a process for recording data thereon and more particularly to an optical data recording medium suitable for recording of data using a multiple photon absorption.

The present invention relates to a two-photon polymerizable composition which induces efficiently two-photon polymerization reaction utilizing two-photon absorption and more particularly to two-photon ultrafine light beam shaping which can prepare a three-dimensional ultrafine structure by photopolymerization attributed to high space resolution of two-photon absorption.

BACKGROUND OF THE INVENTION

In general, a material absorbs one photon having an energy corresponding to excitation energy but does not absorb a photon having an energy which is not within this energy. However, when the intensity of light beam is very strong, two photons the sum of energy of which corresponds to excitation energy can be absorbed at the same time (non-resonant two-photon absorption). The utilization of this nature makes it possible to cause photoreaction only in the vicinity of focus at which light is focused by lens. Thus, an arbitrary position in a space can be selected to develop excited state.

As applications utilizing excited state obtained by non-resonant two-photon absorption there are known three-dimensional optical recording, two-photon microscopic imaging, optical medicare (photodynamic therapy: PDT) and two-photon microfabrication. In particular, two-photon microfabrication makes the best use of the advantage that the spatial resolution of non-resonant two-photon absorption is very high to cause polymerization reaction in a very small space, making it possible to prepare a minute three-dimensional structure.

However, non-resonant two-photon absorption can occur very difficultly. The two-photon absorption cross-section indicating the easiness of two-photon absorption is normally as very small as several GM (GM=$1\times10^{-50}$ cm$^4$s molecule$^{-1}$ photon$^{-1}$). Accordingly, all various applications utilizing non-resonant two-photon absorption have an extremely low sensitivity and thus require a high power laser. This greatly impedes the application of non-resonant two-photon absorption.

In recent years, compounds having a relatively large non-resonant two-photon absorption cross-section have been reported. Examples of two-photon microfabrication using these compounds are described in B. H. Cumpston et al., "Nature", 1999, 398, 51, K. D. Belfield et al., "J. Phys. Org. Chem.", 2000, 13, 837, etc.

However, these examples are disadvantageous in that since usable lasers have a wavelength range as narrow as from 730 nm to 800 nm, efficient two-photon polymerization can be effected only with extremely limited two-photon absorption materials adapted for the wavelength range. Further, most of the compounds exemplified in these references can be difficultly synthesized and have a poor stability.

As a recording medium for recording data with laser beam there has heretofore been known an optical disc such as CD-R and CD-RW. These optical discs employ a laser having a wavelength of about 780 nm. With the recent rapid development of data engineering, there has been a growing demand for recording media having a high capacity and density. In order to realize higher capacity and recording density, it is effective to reduce the diameter of laser beam for data recording as much as possible. However, the diameter of laser beam cannot be reduced beyond diffraction limit. It has been theoretically known that diffraction limit depends on the wavelength of laser beam and the shorter the wavelength of laser beam is, the smaller is diffraction limit. Thus, an optical disc which allows data recording with a laser beam having a wavelength shorter than 780 nm, which has been heretofore used, has been under development. For example, optical discs called DVD-R and DVD-RW have been proposed. DVD-R and DVD-RW employ a laser having a wavelength of from 600 nm to 700 nm to allow data recording at a higher capacity and density than CD-R and CD-RW. However, the laser technology is on a level such that the wavelength of laser beam has been reduced to around 600 nm at last. It will take much time to further spread short wavelength laser and optimize the constitution of recording media required therefore. To cope with this problem, the utilization of two (multi)-photon absorption process, which is one of non-linear optical effects, has been proposed as a means for obtaining a high capacity and density data recording medium.

Two-photon absorption is a phenomenon that a molecule absorbs two photon simultaneously to undergo excitation. Since such a molecule absorbs an energy as great as twice that of photon corresponding to the wavelength of laser beam with which it is irradiated, it can be excited even by a light beam having a longer wavelength free of linear absorption. Further, since the probability of occurrence of two-photon absorption is proportional to second power of intensity of light with which a material is irradiated, the distribution of intensity of laser beam inducing two-photon absorption has a width as narrow as half-width. This corresponds to further reduction of the diameter of laser beam, which makes it possible to recording data in a radius range smaller than the radium of laser beam with which the material is irradiated. Further, from the three-dimensional standpoint of view, two-photon absorption is induced only in a minute region having a strong laser beam intensity at the focal point of laser beam condensed by lens. Thus, no two-photon absorption occurs at any point falling outside the focus, making it possible to induce selective two-photon absorption in an arbitrary minute space in a three-dimensional space. In other words, data recording and reproducing can be made even in the depth direction of a three-dimensional space. Due to this nature, the utilization of two-photon absorption allows data recording at higher density without using a short wavelength laser in principle.

However, two-photon absorption is a non-linear optical process having an extremely small efficiency. Thus, there is little or no materials which perform efficiently two-photon absorption (compounds having a large two-photon absorption cross-section).

In recent years, some compounds were reported to be organic compounds having a great two-photon absorption cross-section as in B. A. Reinhardt et al., "Chem. Mater. 1998", 10, 1863, M. Albota et al., "Science 1998", 281, 1653, J. D. Bhawalkar et al., "Opt. Commun. 1996", 124, 33, G. S. He et al., "Appl. Phys. Lett. 1995", 67, 3703, G. S. He et al., "Appl. Phys. Lett. 1995", 67, 2433, P. N. Pradad et al., "Nonlinear Optics 1999", 21, 39, G. S. He et al., "Appl. Phys. Lett. 1996", 68, 3549, G. S. He et al., "J. Appl. Phys. 1997", 81, 2529, L. -Z. Wu et al., "Chem. Phys. Lett. 1999", 315, 379, S. -J. Chung et al., "J. Phys. Chem. B 1999", 103, 10741, G. S. He et al., "Opt. Lett. 1995", 20, 435, and J. W. Perry et al., "Nonlinear Optics", 1999, 21, 225.

These papers contain compounds having a two-photon absorption cross-section several times to thousands of times that of the conventional compounds. However, none of recording materials comprising these compounds have even been applied.

Further, non-linear optical effect is a non-linear optical response proportional to second, third or higher power of photoelectric field applied. As second order non-linear optical effects proportional to second power of photoelectric field applied there are known second harmonic generation (SHG), photorectification, photorefractive effect, Pockelse effect, parametric amplification, parametric oscillation, optical sum-frequency generation, optical difference frequency generation, etc. As third order non-linear optical effects proportional to third power of photoelectric field applied there are known third harmonic generation (THG), optical Kerr effect, self-focusing, self-defocusing, two-photon absorption, etc.

As non-linear optical materials exerting these non-linear optical effects there have been found numeral inorganic materials. However, such inorganic non-linear optical materials can be very difficultly put to practical use because they can be difficultly molecularly designed for desired non-linear optical properties or optimization of physical properties required for production of element. On the other hand, organic non-linear optical materials can be molecularly designed to not only optimize desired non-linear optical properties but also control other physical properties and thus have been noted as favorable non-linear optical materials which can be fairly put to practical use.

In recent years, among the non-linear optical properties of organic compounds, third order non-linear optical effects have been noted. Among these third order non-linear optical effects, non-resonant two-photon absorption and non-resonant two-photon absorption induced emission have been noted. Two-photon absorption is a phenomenon that a compound absorbs two photons simultaneously to undergo excitation. A phenomenon that two photons are absorbed in an energy region free of (linear) absorption band of compound is called non-resonant two-photon absorption. The non-resonant two-photon absorption induced emission is light emission which occurs in radiative relaxation process followed by non-resonant two-photon absorption.

Now, hereafter, the terms "two-photon absorption" and "two-photon emission" means "non-resonant two-photon absorption" and "non-resonant two-photon absorption induced emission", even if not defined clearly.

The efficiency of non-resonant two-photon absorption is proportional to the square of photoelectric field applied (quadratic dependency on the incident intensity). Thus, when a two-dimensional plane is irradiated with laser beam, the absorption of two-photon occurs only at a position having a high electric field intensity in the central position in the laser spot while no absorption of two-photon occurs at a position having a low electric field intensity out of focus. In a three-dimensional space, on the other hand, two-photon absorption occurs only in a region having a high electric field intensity at the focus obtained by condensing laser beam through lens while no two-photon absorption occurs in other regions falling outside the focus because their electric field intensity is low. As compared with linear absorption in which excitation occurs at all positions in proportion to the intensity of photoelectric field applied, non-resonant two-photon absorption involves excitation only at one point in a space due to the aforementioned second power dependency characteristics and thus provides a remarkably improved spatial resolution. In general, in the case where non-resonant two-photon absorption is induced, a near infrared short pulse laser having a wavelength longer than the wavelength region where the (linear) absorption band of a compound is present and free of absorption is often used. Since a so-called transparent near infrared light free of (linear) absorption band of a compound is used, the excited light can reach the interior of the sample without being absorbed or scattered, making it possible to excite the interior of the sample at one point at an extremely high spatial resolution due to the second power dependency characteristics of two-photon absorption. Thus, non-resonant two-photon absorption and non-resonant two-photon absorption induced emission have been expected for application to two-photon imaging or two-photon photodynamic therapy (PDT) of living tissue. Further, since the use of non-resonant two-photon absorption or non-resonant two-photon absorption induced emission makes it possible to withdraw photons having a higher energy than that of incident photons, studies have been reported of upconversion lasing from the standpoint of wavelength conversion devices.

As an organic compound which performs efficiently two-photon absorption induced light emission or upconversion lasing there is known a so-called stilbazolium derivative (He, G. S. et al., "Appl. Phys. Lett. 1995", 67, 3703, He, G. S. et al., "Appl. Phys. Lett. 1995", 67, 2433, He, G. S. et al., "Appl. Phys. Lett. 1996", 68, 3549, He, G. S. et al., "Appl. Phys. Lett. 1997", 81, 2529, Prasad, P. N. et al., "Nonlinear Optics 1999", 21, 39, Ren, Y. et al., "J. Mater. Chem. 2000", 10, 2025, Zhou, G. et al., "Jpn. J. Appl. Phys. 2001, 40, 1250). Examples of application using two-photon absorption phenomenon of stilbazolium derivative having the specific structure are described in International Patent Publication WO9709043.

In the case where non-resonant two-photon absorption induced (light) emission is applied to imaging of living tissue, photodynamic therapy, upconversion lasing, optical limiting, etc., it is necessary that the organic compound have a high two-photon absorption induced emission efficiency (two-photon absorption cross-section) and a high two-photon absorption induced emission efficiency from the excitation state occurred by two-photon absorption. In order to obtain a two-photon absorption induced emission intensity as high as twice that of an organic compound, an excited light intensity as high as four times the conventional value is needed to give second power dependent characteristics of two-photon absorption. However, when a living tissue, for example, is irradiated with an excessively strong laser beam, it can be damaged by light or the two-photon light-emitting dye itself undergoes deterioration by light to disadvantage. Accordingly, in order to perform strong two-photon absorption induced (light) emission at a low excitation light intensity, it is necessary that an organic compound which performs two-photon absorption and two-photon absorption induced emission efficiently be developed. The two-photon emission efficiency of stilbazolium derivatives has not yet satisfied a level to be desired in actual application.

SUMMARY OF THE INVENTION

An object of the present invention is to provide an organic material which performs efficient two-photon absorption i.e., the organic material having a large two-photon absorption cross-section and the organic material having a large two-photon absorption induced emission intensity.

Another object of the present invention is to provide a high capacity and high density data recording medium using no short wavelength laser beam, a novel data recording process therefor and a novel material for data recording medium for realizing the data recording medium and the data recording process.

As described above, the use of non-resonant two-photon absorption and non-resonant two-photon absorption induced emission makes various applications featuring an extremely high spatial resolution possible. However, two-photon light-emitting compounds which can be used at present exhibit a low two-photon absorbing capacity and a poor two-photon absorption induced emission efficiency and thus requires a very high output laser as an exciting light source for inducing two-photon absorption and two-photon absorption induced emission.

A further object of the present invention is to provide a two-photon polymerizable composition which comprises a two-photon absorbing compound the two-photon absorption wavelength of which can be adjusted for the wavelength of the laser beam used so that laser beam having a wide range of wavelength can be used, exhibits a high two-photon polymerization sensitivity, can be easily synthesized and exhibits an excellent stability and a process for the photopolymerization thereof.

The inventors made extensive studies. As a result, the inventors noted that a compound which can be easily adjusted in two-photon absorption wavelength and has a large two-photon absorption cross-section is important and found that the objects of the present invention can be accomplished by the following constitutions.

(1) A compound represented by the general formula (1) which performs non-resonance two-photon absorption:

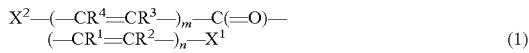

(1)

wherein $X^1$ and $X^2$ may be the same or different, each represent a substituted or unsubstituted aryl group or substituted or unsubstituted heterocyclic group; $R^1$, $R^2$, $R^3$ and $R^4$ each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

(2) A non-resonance two-photon absorption induction method which comprises irradiating a compound represented by the general formula (1) with laser beam having a wavelength longer than the linear absorption band of the compound of the general formula (1) to induce non-resonance two-photon absorption:

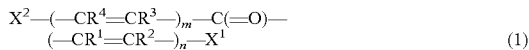

(1)

wherein $X^1$ and $X^2$ may be the same or different, each represent a substituted or unsubstituted aryl group or substituted or unsubstituted heterocyclic group; $R^1$, $R^2$, $R^3$ and $R^4$ each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

(3) A two-photon light-emitting compound having a structure represented by the following general formula (1):

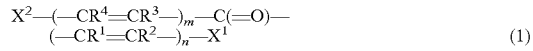

(1)

wherein $X^1$ and $X^2$ may be the same or different, each represent a substituted or unsubstituted aryl group or substituted or unsubstituted heterocyclic group; $R^1$, $R^2$, $R^3$ and $R^4$ each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

(4) A light emitting method which comprises irradiating a compound represented by the general formula (1) with laser beam having a wavelength longer than the linear absorption band of the compound of the general formula (1) to induce non-resonant two-photon absorption, thereby causing light emission from the excitation:

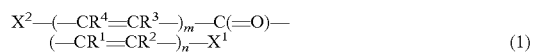

(1)

wherein $X^1$ and $X^2$ may be the same or different, each represent a substituted or unsubstituted aryl group or substituted or unsubstituted heterocyclic group; $R^1$, $R^2$, $R^3$ and $R^4$ each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

(5) An optical data recording medium capable of recording data with a laser beam, which comprises a compound represented by the general formula (1) in the item (1) incorporated therein.

(6) A process for recording data utilizing to the optical data recording medium of claim 3, two-photon or higher multiple photon absorption induced by irradiating a recording medium with a laser beam having a wavelength longer than the linear absorption band of the compound of the general formula (1) in the item (1) and free of linear absorption.

(7) A two-photon polymerizable composition photopolymerizable by two-photon absorption comprising at least a two-photon absorbing material and a polymerizable monomer or polymerizable oligomer, wherein the two-photon absorbing material is a compound represented by the following general formula (1):

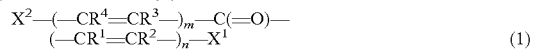

(1)

wherein $X^1$ and $X^2$ may be the same or different, each represent a substituted or unsubstituted aryl group or a substituted or unsubstituted heterocyclic group; $R^1$, $R^2$, $R^3$ and $R^4$, each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

(8) A photopolymerization process which causes polymerization reaction utilizing two-photon or higher multiple photon absorption induced by irradiating a polymerizable composition according to claim 1 with laser beam having a wavelength longer than the linear absorption band of the compound of the general formula (1) in the item (1) and free of linear absorption.

DETAILED DESCRIPTION OF THE INVENTION

Embodiments of the two-photon polymerizable composition according to the present invention will be described hereinafter.

The two-photon polymerizable composition according to the present invention comprises at least a two-photon absorbing material and a polymerizable monomer or polymerizable oligomer, wherein the two-photon absorbing material is a compound represented by the following general formula (1):

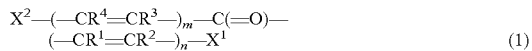
$$X^2-(-CR^4=CR^3-)_m-C(=O)-\\(-CR^1=CR^2-)_n-X^1 \quad (1)$$

wherein $X^1$ and $X^2$ may be the same or different, each represent a substituted or unsubstituted aryl group or a substituted or unsubstituted heterocyclic group; $R^1$, $R^2$, $R^3$ and $R^4$, each independently represent a hydrogen atom or substituent; some of $R^1$, $R^2$, $R^3$ and $R^4$ may be connected to each other to form at least one ring; and n and m, each independently represent an integer of from 1 to 4, with the proviso that when n and m are 2 or more, the plurality of $R^1$'s, $R^2$'s, $R^3$'s, and $R^4$'s each may be the same or different.

The compound represented by the general formula (1) will be further described hereinafter.

In the general formula (1), $X^1$ and $X^2$ each preferably represent a $C_6$-$C_{30}$ substituted or unsubstituted aryl group or $C_1$-$C_{10}$ substituted or unsubstituted heterocyclic group.

The aryl group represented by $X^1$ or $X^2$ in the general formula (1) is preferably a $C_6$-$C_{30}$ substituted or unsubstituted aryl group. Examples of such an aryl group include phenyl, naphthyl, anthracenyl, and phenanthrenyl. Preferred among these aryl groups are phenyl and naphthyl, particularly phenyl.

The heterocyclic group represented by $X^1$ or $X^2$ in the general formula (1) is preferably a $C_1$-$C_{10}$ heterocyclic group. Preferred examples of such a heterocyclic group include a $C_2$-$C_9$ heterocyclic group, particularly a $C_2$-$C_5$ heterocyclic group. Preferred examples of the hetero atom incorporated in the heterocyclic group include nitrogen atom, oxygen atom, and sulfur atom.

Specific examples of the heterocyclic group include pyrrolidine, piperidine, piperazine, morpholine, thiophene, selenophene, furane, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzoimidazole, benzoxazole, benzothiazole, benzotriazole, tetrazaindene, benzoindolene, carbazole, dibenzofurane, and quaternary onium cation having quaterized nitrogen atoms (if nitrogen atoms form a ring). Preferred among these heterocyclic groups are pyridine, pyrimidine, pyrazine, indole, thiophene, thiazole, oxazole, quinoline, acridine, benzoimidazole, benzoxazole, benzothiazole, benzoindolene, and quaternary onium cation having quaterized nitrogen atoms (if nitrogen atoms form a ring). Particularly preferred among these heterocyclic groups are pyridine, thiophene, acridine, benzoimidazole, benzoxazole, benzothiazole, benzoindolene, and quaternary onium cation having quaterized nitrogen atoms (if nitrogen atoms form a ring).

$X^1$ and $X^2$ in the general formula (1) may further have substituents. Examples of these substituents include $C_1$-$C_{20}$ linear or cyclic alkyl groups such as methyl, ethyl, n-propyl, isopropyl and n-butyl, $C_6$-$C_{18}$ substituted or unsubstituted aryl groups such as phenyl, chlorophenyl, anisyl, toluil and 1-naphthyl, $C_2$-$C_{20}$ alkenyl groups such as vinyl and 2-methylvinyl, $C_2$-$C_{20}$ alkynyl groups such as ethyniyl, 2-methylethynyl and 2-phenylethynyl, halogen atoms such as F, Cl, Br and I, $C_2$-$C_{20}$ amino groups such as dimethylamino, diethylamino, dibutylamino and julolidino, cyano groups, hydroxyl groups, carboxyl groups, $C_2$-$C_{10}$ acyl groups such as acetyl, benzoyl, salicyloyl and pivaloyl, $C_1$-$C_{20}$ alkoxy groups such as methoxy, butoxy and cyclohexyloxy, $C_6$-$C_{18}$ aryloxy groups such as phenoxy and 1-naphthoxy, $C_1$-$C_{20}$ alkylthio groups such as methylthio and ethylthio, $C_6$-$C_{18}$ arylthio groups such as phenylthio and 4-chlorophenylthio, $C_1$-$C_{20}$ alkylsulfonyl groups such as methanesulfonyl and butanesulfonyl, $C_6$-$C_{18}$ arylsulfonyl groups such as benzenesulfonyl and paratoluenesulfonyl, $C_1$-$C_{10}$ carbamoyl groups, $C_1$-$C_{10}$ amide groups, $C_2$-$C_{12}$ imide groups, $C_2$-$C_{10}$ acyloxy groups, $C_2$-$C_{10}$ alkoxycarbonyl groups, and $C_1$-$C_{10}$ heterocyclic groups such as aromatic heterocyclic group (e.g., pyridyl, chenyl, furyl, thiazolyl, imidazolyl, pyrazolyl) and aliphatic heterocyclic group (e.g., pyrolidine ring, piperidine ring, morpholine ring, pyrane ring, thiopyrane ring, dioxane ring, dithiolane ring).

Preferred examples of the substituents on $X^1$ and $X^2$ in the general formula (1) include $C_1$-$C_{16}$ linear or cyclic alkyl groups, $C_6$-$C_{14}$ aryl groups, $C_7$-$C_{15}$ aralkyl groups, $C_1$-$C_{16}$ alkoxy groups, $C_6$-$C_{14}$ aryloxy groups, $C_2$-$C_{20}$ amino groups, halogen atoms, $C_2$-$C_{17}$ alkoxycarbonyl groups, $C_1$-$C_{10}$ carbamoyl groups, $C_1$-$C_{10}$ amide groups, and $C_2$-$C_{10}$ heterocyclic groups. Particularly preferred among these substituents are $C_1$-$C_{10}$ linear or cyclic alkyl groups, $C_7$-$C_{13}$ aralkyl groups, $C_6$-$C_{10}$ aryl groups, $C_1$-$C_{10}$ alkoxy groups, $C_6$-$C_{10}$ aryloxy groups, $C_2$-$C_{10}$ amino groups, chlorine atom, bromine atom, $C_2$-$C_{11}$ alkoxycarbonyl groups, $C_1$-$C_7$ carbamoyl groups, and $C_1$-$C_8$ amide groups.

In the general formula (1), $R^1$, $R^2$, $R^3$ and $R^4$, each independently represent a hydrogen atom or substituent. Some of $R^1$, $R^2$, $R^3$ and $R^4$ may be connected to each other to form a ring.

A preferred example of the cyclic structure formed by $R^1$, $R^2$, $R^3$ and $R^4$ is a 5-, 6- or 7-membered, more preferably 5- or 6-membered ring, formed by ethylene, propylene or butylene group formed by $R^1$ and $R^3$.

In case substituents represented by $R^1$, $R^2$, $R^3$ and $R^4$ in the general formula (1) are substituted by another group, examples of the group include those exemplified as a substituent represented by $X^1$ and $X^2$.

In the general formula (1), any two of the substituents represented by $R^1$, $R^2$, $R^3$ and $R^4$ may be connected to each other to form a ring. In the case where any two of the substituents represented by $R^1$, $R^2$, $R^3$ and $R^4$ are connected to each other to form a ring, it is preferred that $R^1$ and $R^3$ connected to the carbon atom connected to the carbonyl carbon atom in the central portion of the general formula (1) be connected to each other to form a ring.

In the case where $R^1$ and $R^3$ are connected to each other to form a ring in the general formula (1), the resulting ring is preferably a four-, five- or six-membered ring, most preferably four- or five-membered ring.

In the general formula (1), when n and m, each are 2 or more, the plurality of $R^1$'s, $R^2$'s, $R^3$'s, and $R^4$'s each may be the same or different.

In the general formula (1), n and m, each independently represent an integer of from 1 to 5, preferably from 2 to 4.

The two-photon absorbing compound of the present invention is synthesized by the aldol condensation reaction of ketone compound with aldehyde compound.

Specific examples of the compound represented by the general formula (1) to be used herein will be given below, but the present invention is not limited thereto.

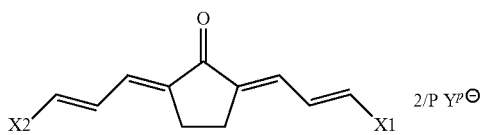
| Compound No. | X1 | X2 | $Y^{p\ominus}$ |
|---|---|---|---|
| (1) | 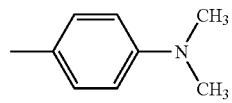 | 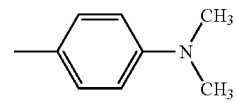 | — |
| (2) | 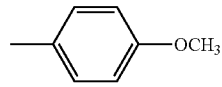 |  | — |
| (3) | 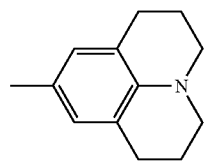 | 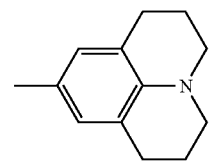 | — |
| (4) | 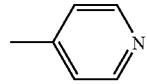 | 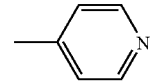 | — |
| (5) |  |  | — |
| (6) |  |  | — |
| (7) |  |  | — |
| (8) | 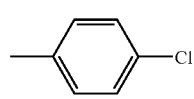 |  | — |
| (9) | 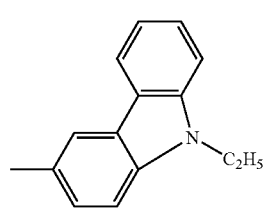 | 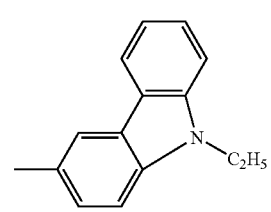 | — |
| (10) |  |  | — |
| (11) | 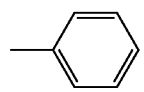 | 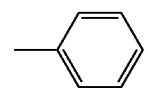 | — |
| (12) | 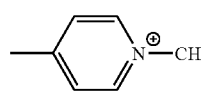 | 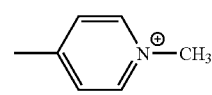 | $ClO_4^{\ominus}$ |

-continued
| Compound No. | | | |
|---|---|---|---|
| (13) | 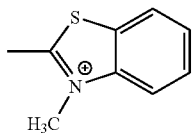 | 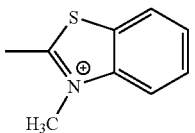 | PF$_6^\ominus$ |
| (14) | 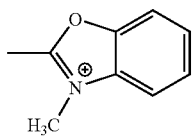 | 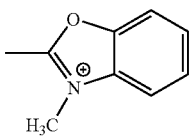 | 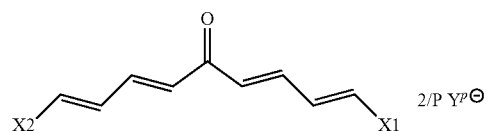 H$_3$C—⟨⟩—SO$_3^\ominus$ |
| (A01) | 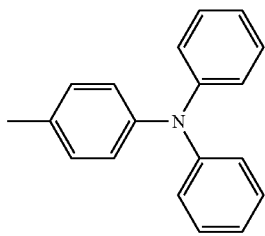 | 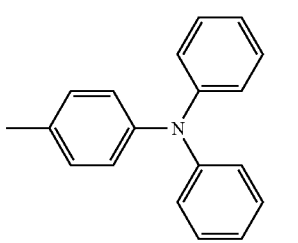 | — |
| (A02) | 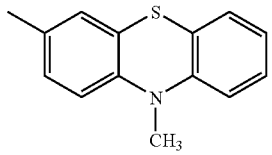 | 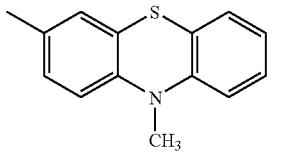 | — |
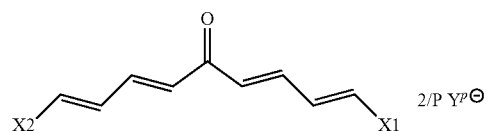
| Compound No. | X1 | X2 | Y$^{p\ominus}$ |
|---|---|---|---|
| (15) | 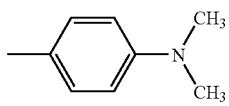 | 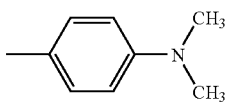 | — |
| (16) | 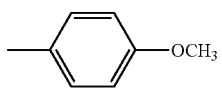 | 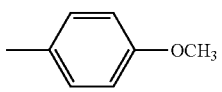 | — |
| (17) | 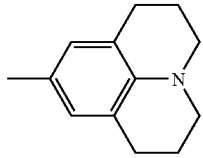 | 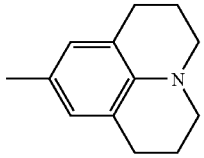 | — |
| (18) | 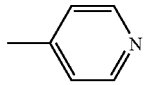 | 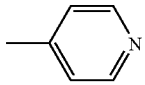 | — |
| (19) | 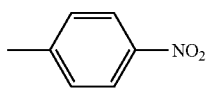 | 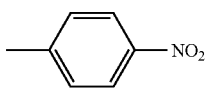 | — |
| (20) | 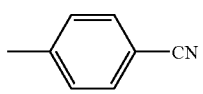 | 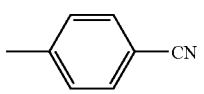 | — |

-continued
| | | | |
|---|---|---|---|
| (21) | 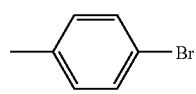 | 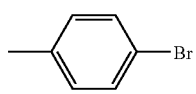 | — |
| (22) | 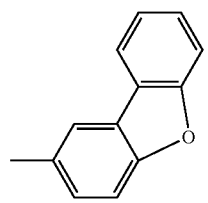 | 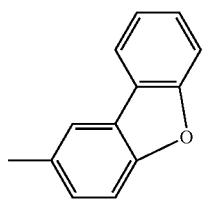 | — |
| (23) | 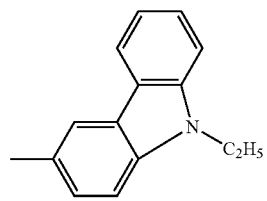 | 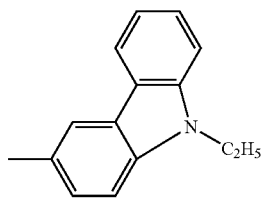 | — |
| (24) | 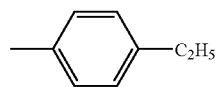 | 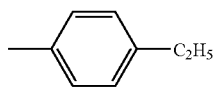 | — |
| (25) | 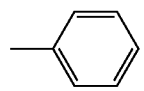 | 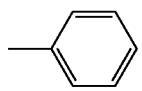 | — |
| (26) | 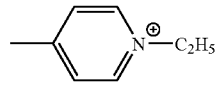 | 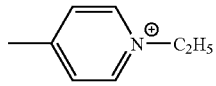 | $I^{\ominus}$ |
| (27) | 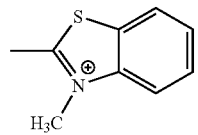 | 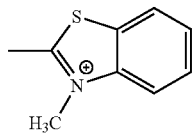 | $PF_6^{\ominus}$ |
| (28) | 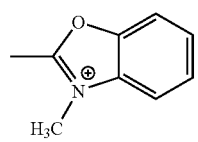 | 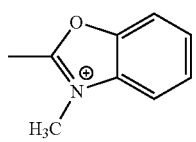 | $ClO_4^{\ominus}$ |
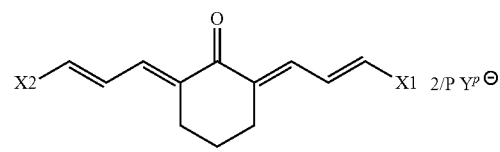
| Compound No. | X1 | X2 | $Y^{p\ominus}$ |
|---|---|---|---|
| (29) | 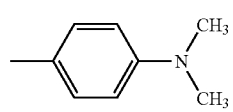 | 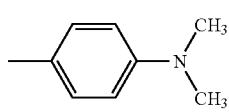 | — |
| (30) | 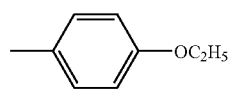 | 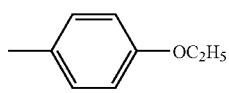 | — |

-continued
| | | | |
|---|---|---|---|
| (31) | 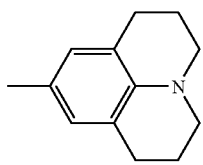 | 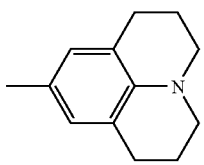 | — |
| (32) | 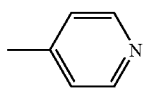 | 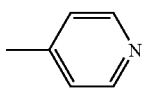 | — |
| (33) | 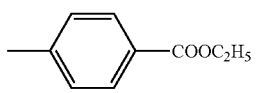 | 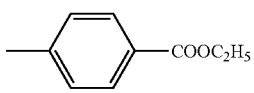 | — |
| (34) | 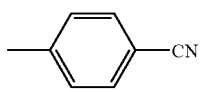 | 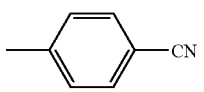 | — |
| (35) | 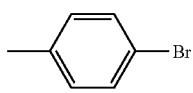 | 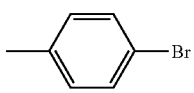 | — |
| (36) | 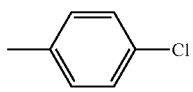 | 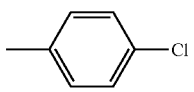 | — |
| (37) |  | 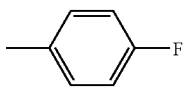 | — |
| (38) | 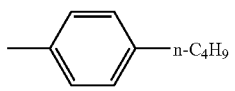 | 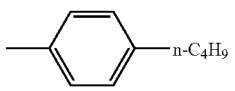 | — |
| (39) | 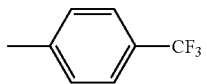 | 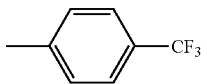 | — |
| (40) | 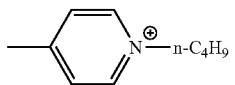 | 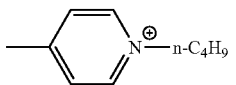 | Br$^{\ominus}$ |
| (41) | 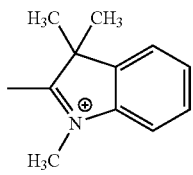 | 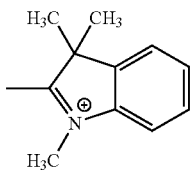 | ClO$_4^{\ominus}$ |
| (42) | 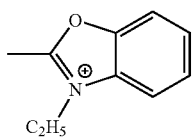 | 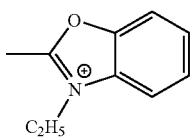 | PF$_6^{\ominus}$ |

-continued
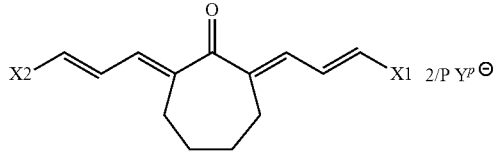
| Compound No. | X1 | X2 | Y$^{p\ominus}$ |
|---|---|---|---|
| (43) | 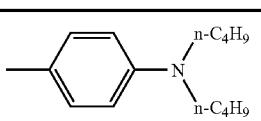 |  | — |
| (44) | 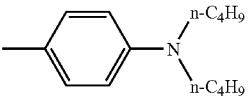 | 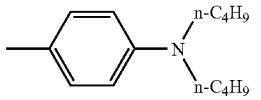 | — |
| (45) | 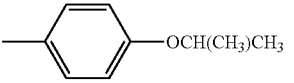 | 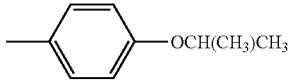 | — |
| (46) | 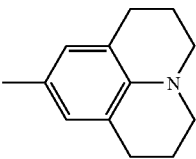 | 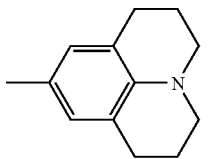 | — |
| (47) | 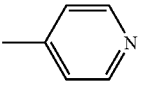 | 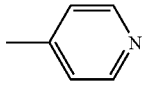 | — |
| (48) | 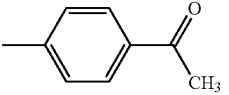 | 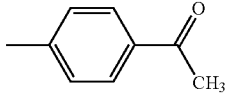 | — |
| (49) | 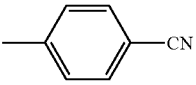 | 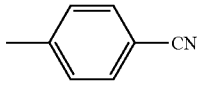 | — |
| (50) | 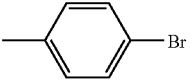 | 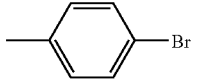 | — |
| (51) | 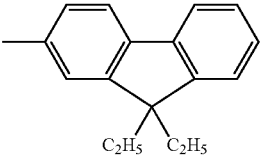 | 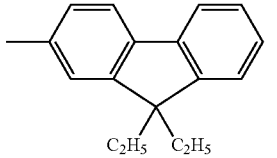 | — |
| (52) |  |  | — |
| (53) | 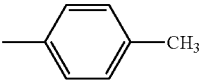 | 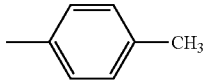 | — |
| (54) | 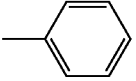 | 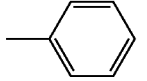 | ClO$_4^\ominus$ |

-continued
| | | | |
|---|---|---|---|
| (55) | 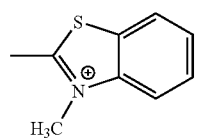 | 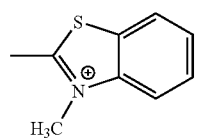 | PF$_6^\ominus$ |
| (56) | | | I$^\ominus$ |
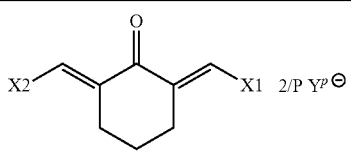
| Compound No. | X1 | X2 | Y$^{p\ominus}$ |
|---|---|---|---|
| (57) | 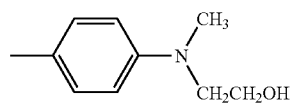 | 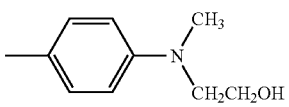 | — |
| (58) | 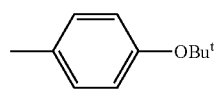 | 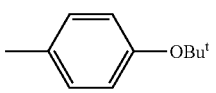 | — |
| (59) | 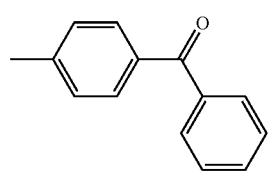 | 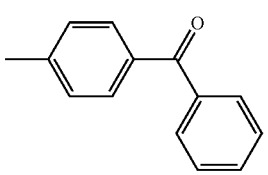 | — |
| (60) | 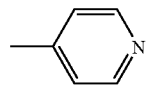 | 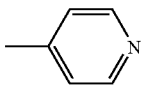 | — |
| (61) | 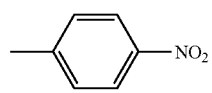 | 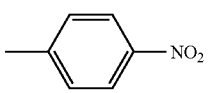 | — |
| (62) | 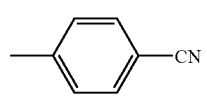 | 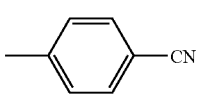 | — |
| (63) | 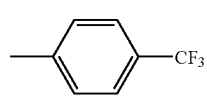 | 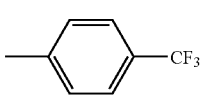 | — |
| (64) | 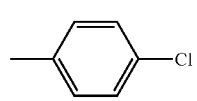 | 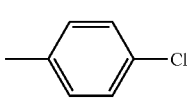 | — |
| (65) | 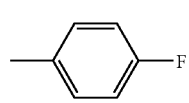 | 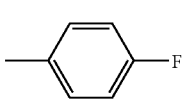 | — |
| (66) | 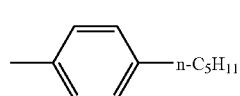 | 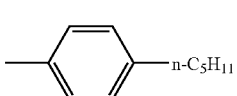 | — |

-continued
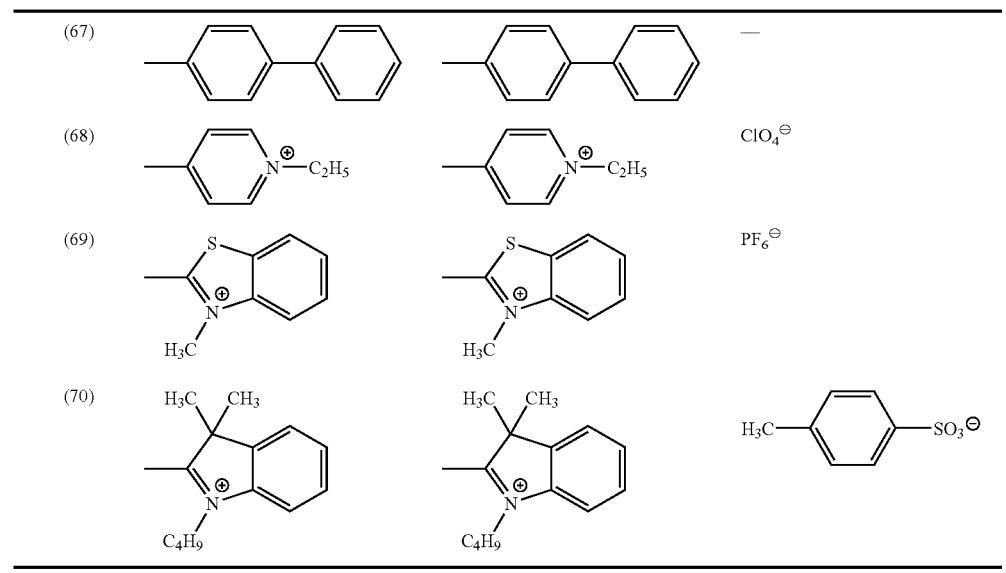
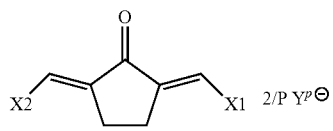
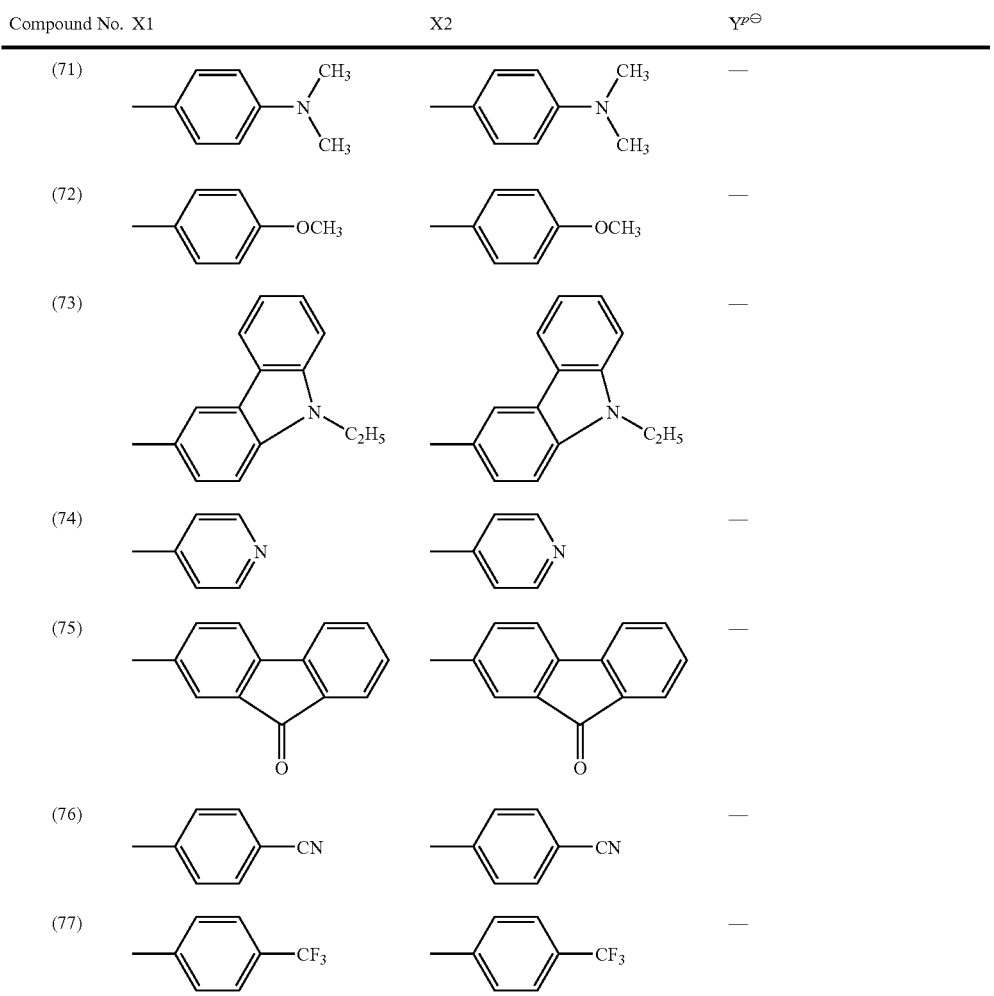

-continued
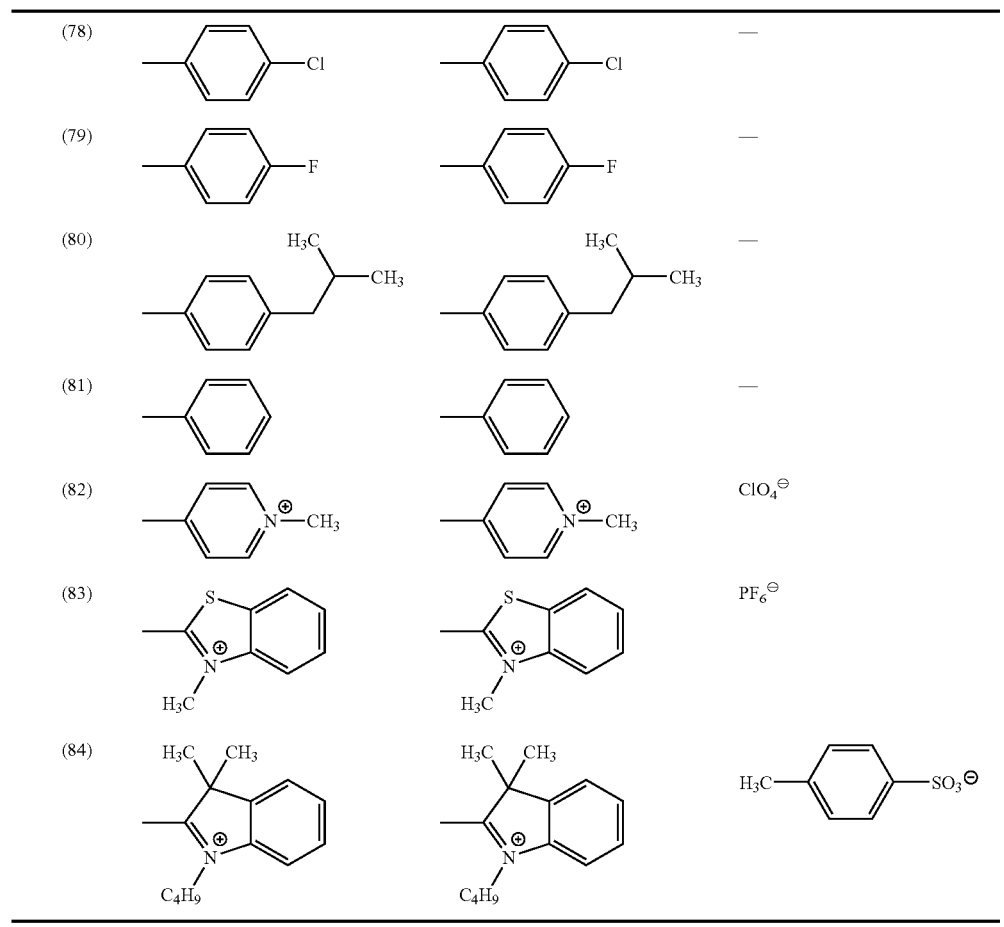
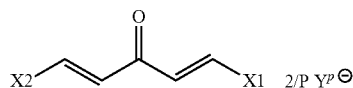
| Compound No. | X1 | X2 | $Y^{p\ominus}$ |
|---|---|---|---|
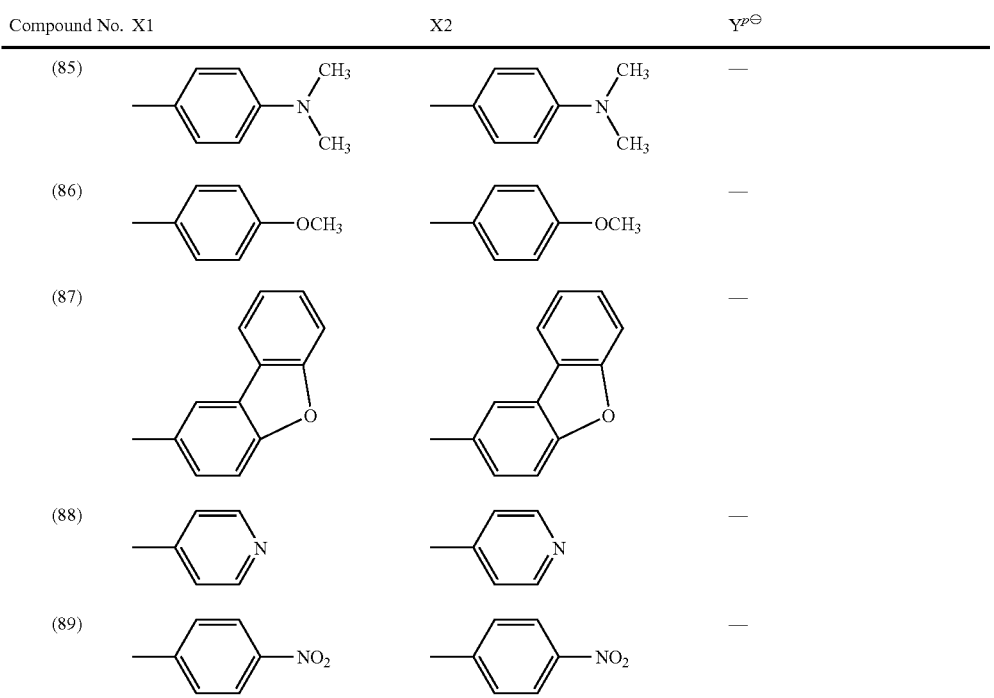

-continued
| Compound No. | X1 | X2 | Y |
|---|---|---|---|
| (90) | 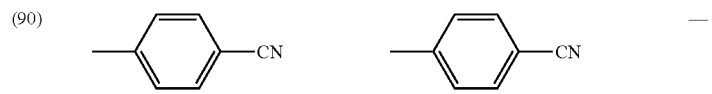 | | — |
| (91) | 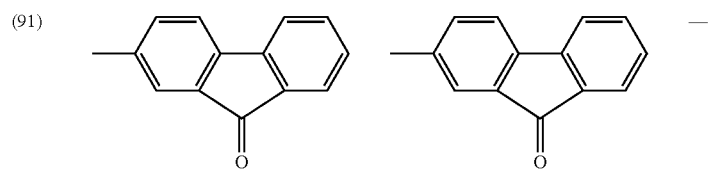 | | — |
| (92) |  | | — |
| (93) | 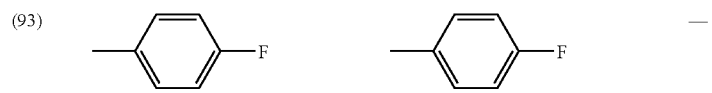 | | — |
| (94) | 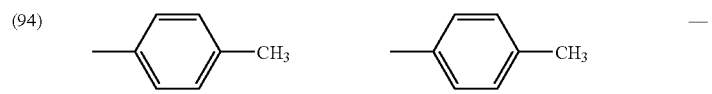 | | — |
| (95) |  | | — |
| (96) | 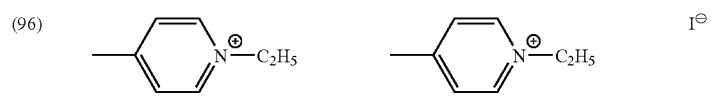 | | $I^\ominus$ |
| (97) | 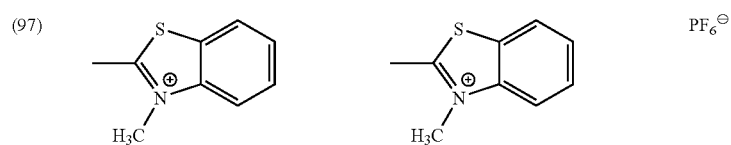 | | $PF_6^\ominus$ |
| (98) | 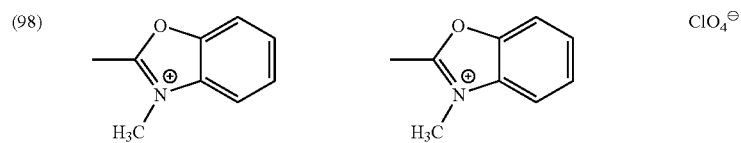 | | $ClO_4^\ominus$ |
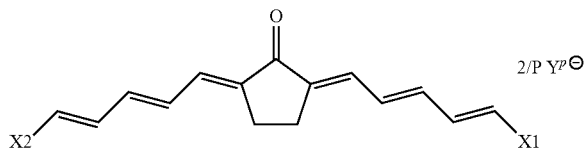
| Compound No. | X1 | X2 | $Y^{p\ominus}$ |
|---|---|---|---|
| (99) | 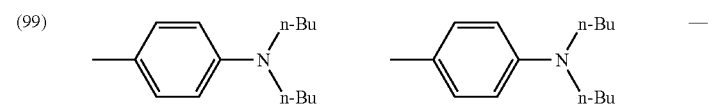 | | — |
| (100) |  | | — |

-continued
(101) 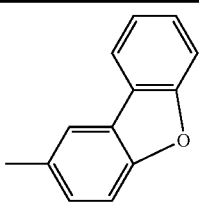 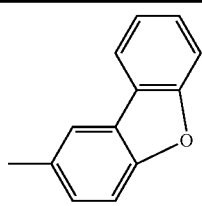 —
(102) 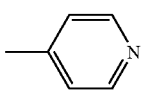 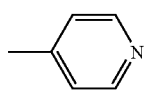 —
(103) 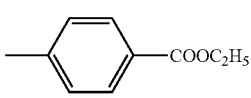 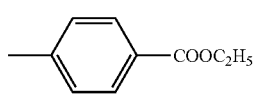 —
(104) 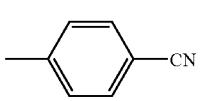  —
(105) 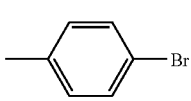  —
(106) 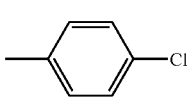  —
(107) 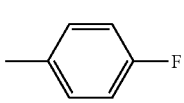  —
(108) 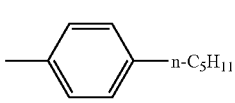 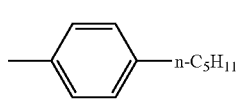 —
(109) 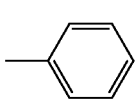 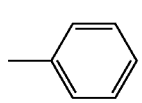 —
(110) 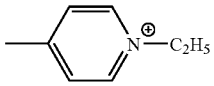  ClO$_4^\ominus$
(111) 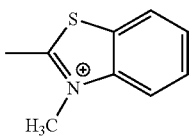 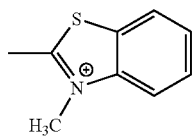 PF$_6^\ominus$
(112) 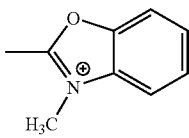 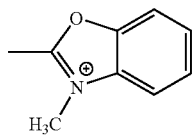 
(A03) 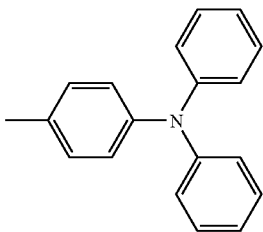 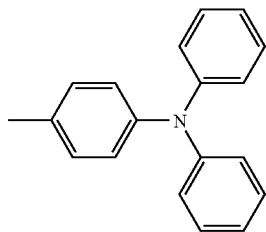 —

| | | | |
|---|---|---|---|
| (A04) | 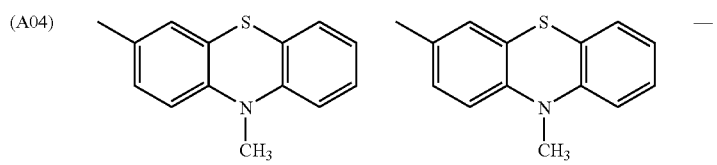 | | — |
| (A05) | 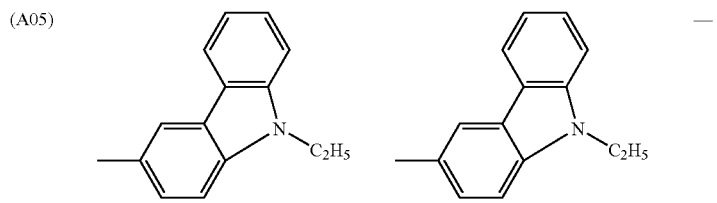 | | — |
| (A06) | 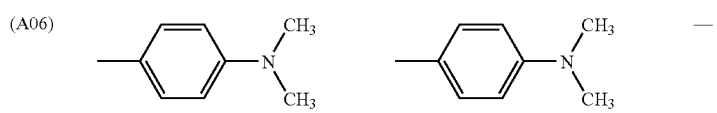 | | — |
| (A07) | 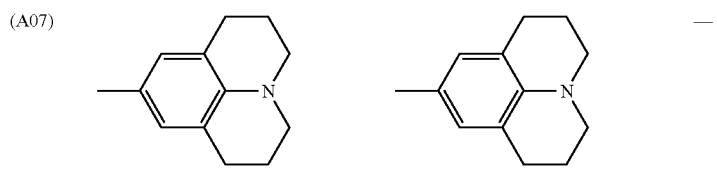 | | — |
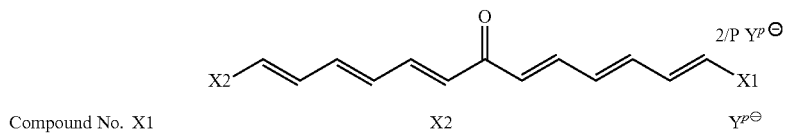
| Compound No. | X1 | X2 | $Y^{p\ominus}$ |
|---|---|---|---|
| (113) | 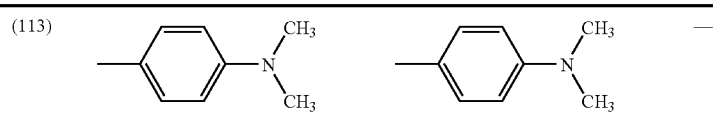 | | — |
| (114) | 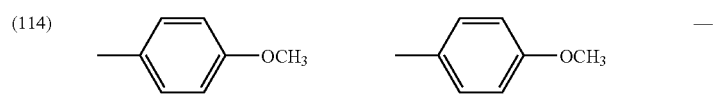 | | — |
| (115) | 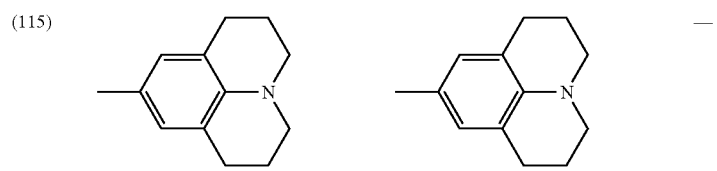 | | — |
| (116) | 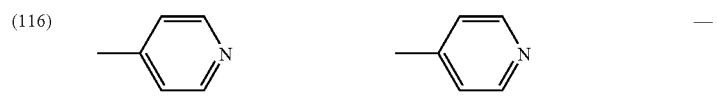 | | — |
| (117) | 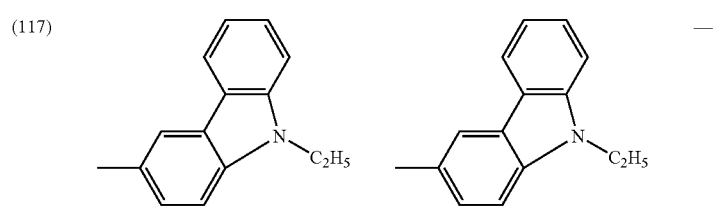 | | — |
| (118) | 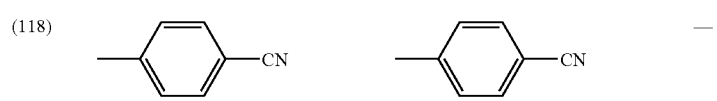 | | — |

-continued
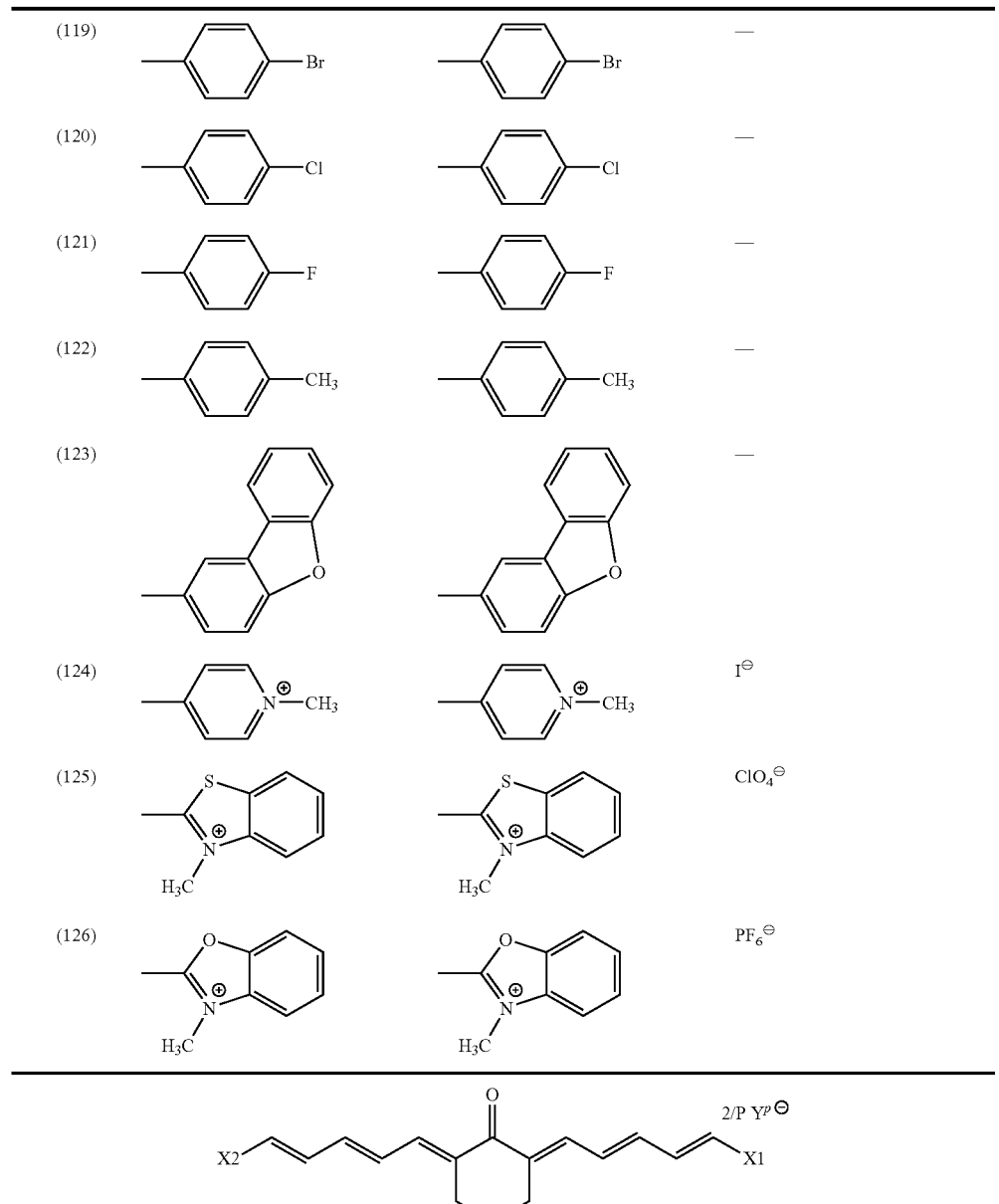
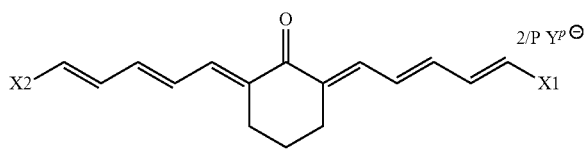
| Compound No. | X1 | X2 | $Y^{p\ominus}$ |
|---|---|---|---|
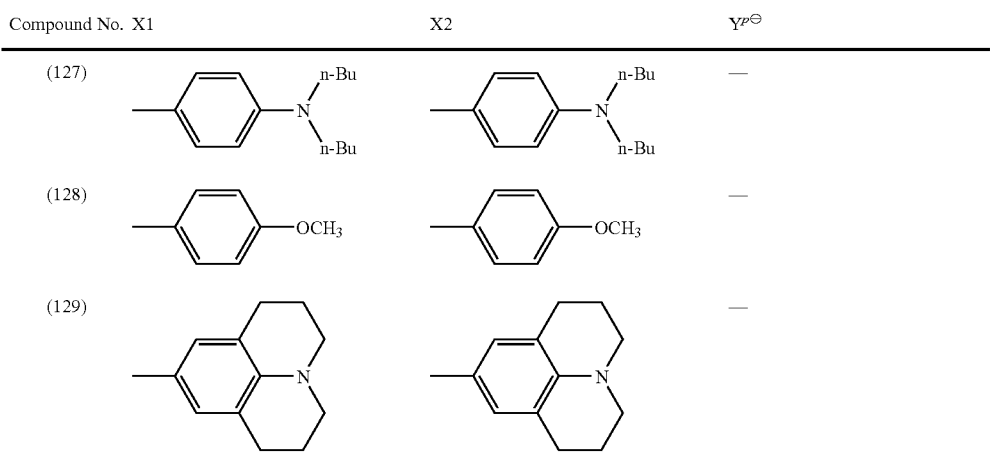

-continued
| | | | |
|---|---|---|---|
| (130) | 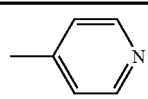 | 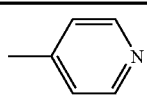 | — |
| (131) | 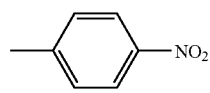 | 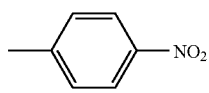 | — |
| (132) | 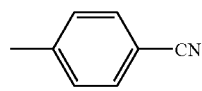 | 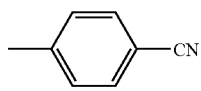 | — |
| (133) | 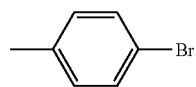 | 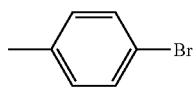 | — |
| (134) | 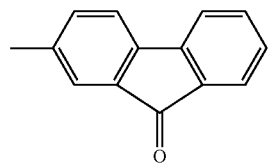 | 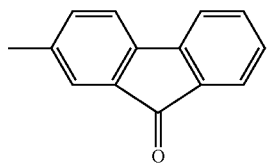 | — |
| (135) |  |  | — |
| (136) | 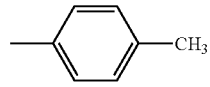 | 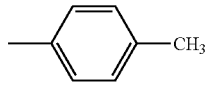 | — |
| (137) | 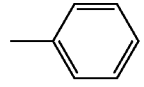 | 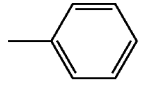 | — |
| (138) |  | 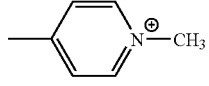 | $ClO_4^{\ominus}$ |
| (139) | 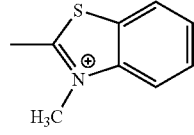 | 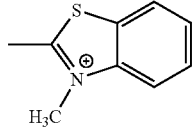 | $PF_6^{\ominus}$ |
| (140) | 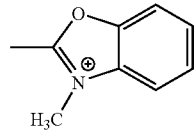 | 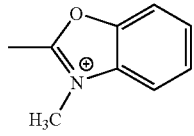 | 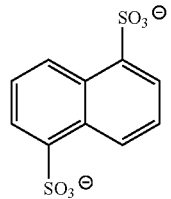 |
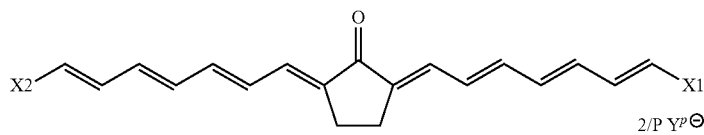
2/P $Y^{p\ominus}$
| Compound No. | X1 | X2 | $Y^{p\ominus}$ |
|---|---|---|---|
| (A08) | 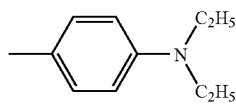 | 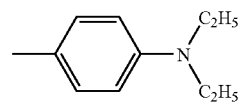 | — |

| | | | |
|---|---|---|---|
| (A09) | 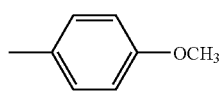 | 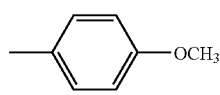 | — |
| (A10) | 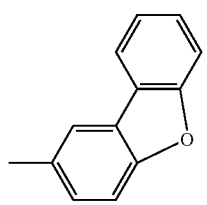 | 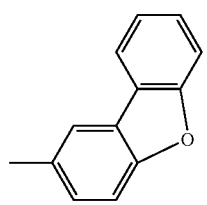 | — |
| (A11) | 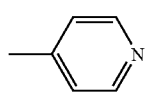 | 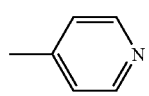 | — |
| (A12) | 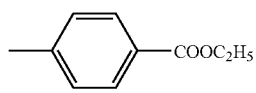 | 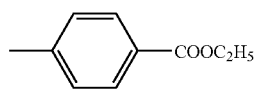 | — |
| (A13) | 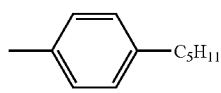 | 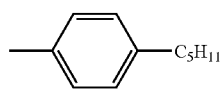 | — |
| (A14) | 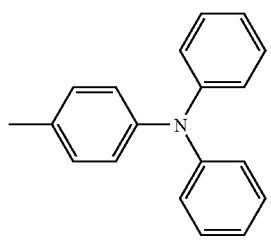 | 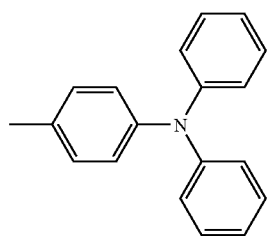 | — |
| (A15) | 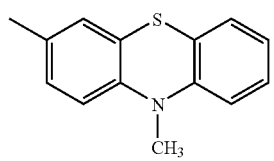 | 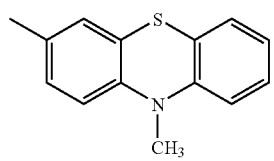 | — |
| (A16) | 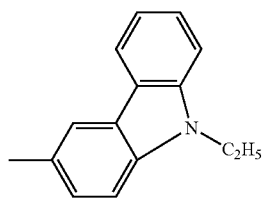 | 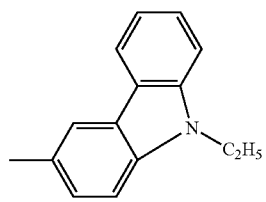 | — |
| (A17) | 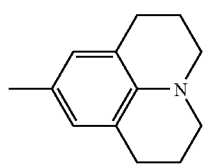 | 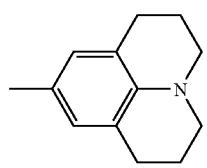 | — |

-continued
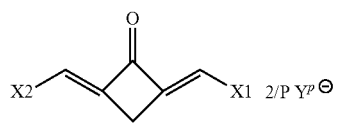
| Compound No. | X1 | X2 | Y^{p⊖} |
|---|---|---|---|
| (A18) | —C6H4—N(C2H5)2 | —C6H4—N(C2H5)2 | — |
| (A19) | —C6H4—OCH3 | —C6H4—OCH3 | — |
| (A20) | julolidin-9-yl | julolidin-9-yl | — |
| (A21) | pyridin-4-yl | pyridin-4-yl | — |
| (A22) | —C6H4—N(C6H5)2 | —C6H4—N(C6H5)2 | — |
| (A23) | 10-methylphenothiazin-3-yl | 10-methylphenothiazin-3-yl | — |
| (A24) | 9-ethylcarbazol-3-yl | 9-ethylcarbazol-3-yl | — |
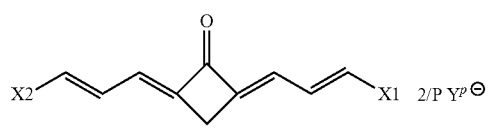
| Compound No. | X1 | X2 | Y^{p⊖} |
|---|---|---|---|
| (A25) | —C6H4—N(C2H5)2 | —C6H4—N(C2H5)2 | — |

-continued
| | | | |
|---|---|---|---|
| (A26) | 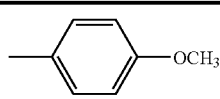 | 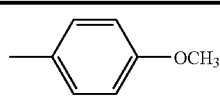 | — |
| (A27) | 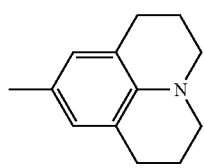 | 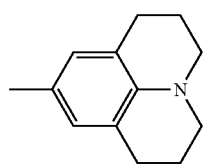 | — |
| (A28) | 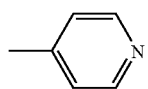 | 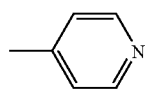 | — |
| (A29) | 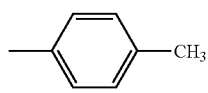 | 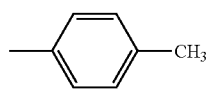 | — |
| (A30) | 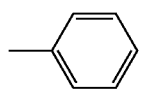 | 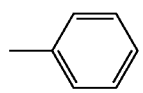 | — |
| (A31) | 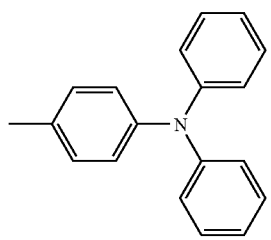 | 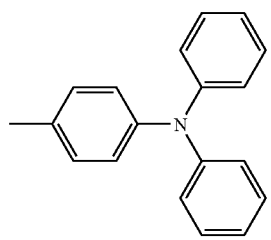 | — |
| (A32) | 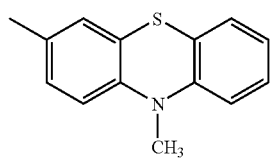 | 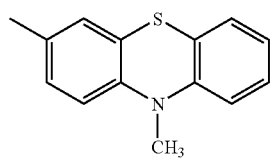 | — |
| (A33) | 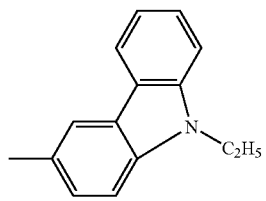 | 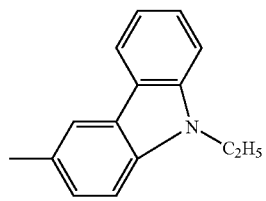 | — |
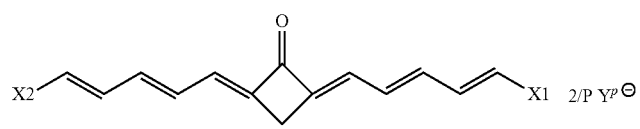
| Compound No. | X1 | X2 | $Y^{p\ominus}$ |
|---|---|---|---|
| (A34) | 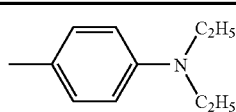 | 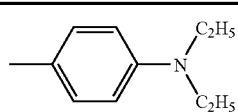 | — |
| (A35) | 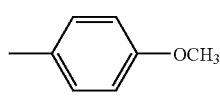 | 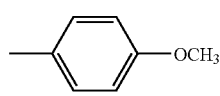 | — |

-continued
| Compound No. | X1 | X2 | |
|---|---|---|---|
| (A36) | 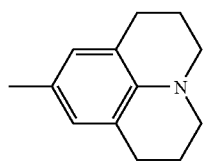 | 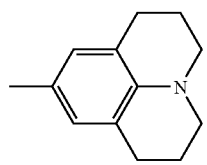 | — |
| (A37) | 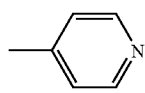 | 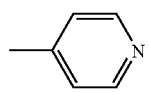 | — |
| (A38) | 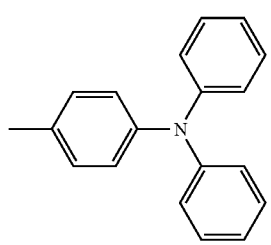 | 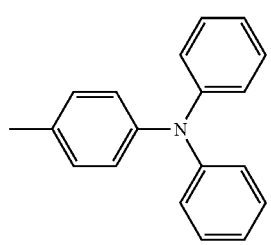 | — |
| (A39) | 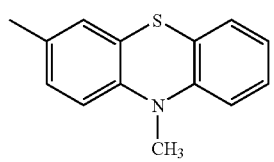 | 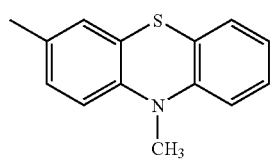 | — |
| (A40) | 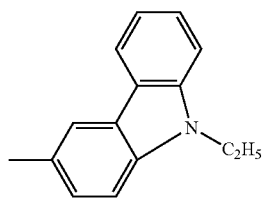 | 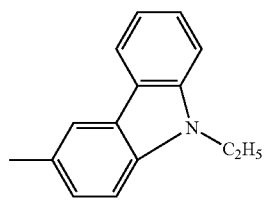 | — |
| (A41) | 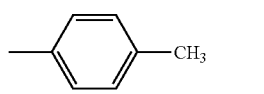 | 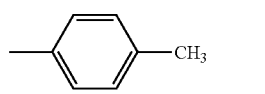 | — |
X2—⟨chain⟩—X1   2/P Y$^{p\ominus}$
| Compound No. | X1 | X2 | Y$^{p\ominus}$ |
|---|---|---|---|
| (A42) | 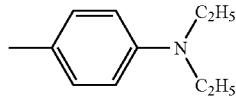 | 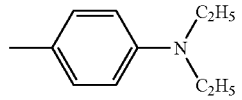 | — |
| (A43) | 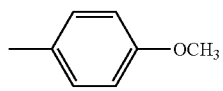 | 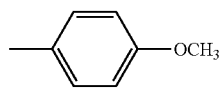 | — |
| (A44) | 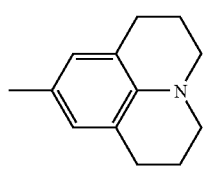 | 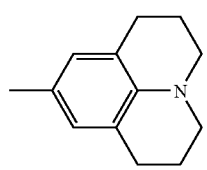 | — |
| (A45) | 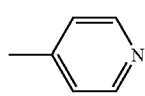 | 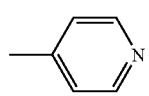 | — |

| | | |
|---|---|---|
| (A46) | 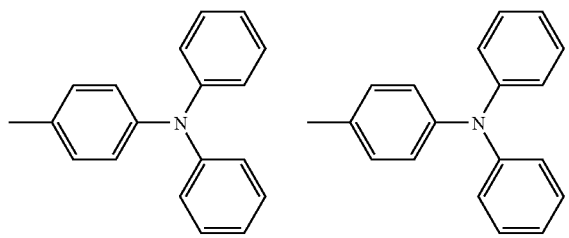 | — |
| (A47) | 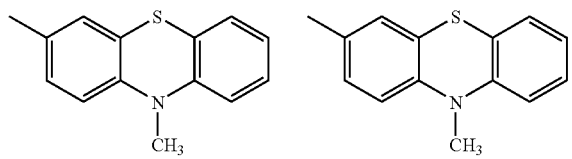 | — |
| (A48) | 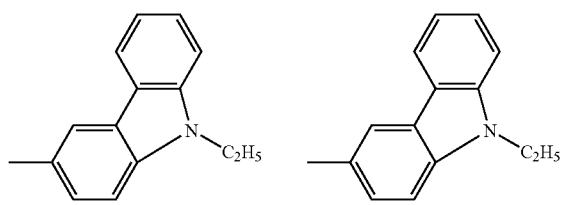 | — |
| (A49) |  | — |

Specific examples of synthesis of the two-photon absorbing compound will be given below. In some detail, examples of synthesis of the compound represented by the general formula (1) will be described.

Synthesis Example 1

Synthesis of Compound (1)

17.5 g (0.1 mol) of p-(dimethylamino) cinnamaldehyde and 4.2 g (0.05 mol) of cyclopentanone were dissolved in 2.4 l of isopropyl alcohol. To the solution was then added 1 ml of a methanol solution of sodium methoxide, and the reaction mixture was then stirred for 1 hour at 40° C. The precipitated solids were collected, and recrystallized from chloroform-methanol. A dark reddish crystal was obtained in an amount of 11.0 g (yield: 55%). The compound thus obtained was characterized by $^1$H NMR.

$^1$H NMR (CDCl$_3$-d$_1$)

$\delta$=2.86 (s, 4H, cyclopentane ring), 3.01 (s, 12H, dimethylamine group), 6.67 (d, 4H, benzene ring), 7.39 (d, 4H, benzene ring), 6.76 (t, 2H, methine chain), 6.90 (d, 2H, methine chain), 7.24 (d, 2H, methine chain)

Synthesis Example 2

Synthesis of Compound (15)

Compound (15) was synthesized in the same manner as in Synthesis Example 1 except that acetone (2.9 g, 0.05 mol) was used instead of cyclopentanone. Thus, a dark reddish crystal was obtained in an amount of 3.8 g (yield: 20%). The compound thus obtained was confirmed for its structure by $^1$H NMR.

$^1$H NMR (CDCl$_3$-d$_1$)

$\delta$=3.01 (s, 12H, dimethylamino group), 6.67 (d, 4H, benzene ring), 7.38 (d, 4H, benzene ring), 6.46 (d, 2H, methine chain), 6.76 (m, 2H, methine chain), 6.90 (d, 2H, methine chain), 7.48 (m, 2H, methine chain)

Synthesis Example 3

Synthesis of Compound (29)

Compound (29) was synthesized in the same manner as in Synthesis Example 1 except that cyclohexanone (4.9 g, 0.05 mol) was used instead of cyclopentanone. Thus, a dark reddish crystal was obtained in an amount of 7.2 g (yield: 35%). The compound thus obtained was confirmed for its structure by $^1$H NMR.

$^1$H NMR (DMSO-d$_6$)

$\delta$=1.85 (m, 2H, cyclohexane ring), 2.75 (t, 4H, cyclohexane ring), 3.00 (s, 12H, dimethylamino group), 6.66 (d, 4H, benzene ring), 7.39 (d, 4H, benzene ring), 6.89 (m, 4H, methine chain), 7.50 (d, 2H, methine chain)

Examples of the polymerizable monomer or polymerizable oligomer to be used herein include radical polymerizable compounds such as acrylic acid ester and acrylonitrile-based compound, and cation polymerizable compounds such as vinyl ether, methylene dioxolane and epoxide. In particular, epoxy-based compounds are preferred as optical shaping liquid photosetting resin because they have a relatively small volume shrinkage. Urethane acrylates are more desirable from the standpoint of thermal properties and mechanical properties.

Specific examples of the photosetting resin employable herein include HS-681, DMS-SOMOS and SOMOS8100 (produced by ASAHI DENKA KOGYO K.K.), SCR-8100 Series (produced by JSR Corporation), epoxy resins such as SL-7540 (produced by Vantico Co., Ltd.), SCR-710 (produced by D-MEC LTD.), and urethane acrylates such as TSR-1938 (produced by TEIJIN LTD.).

The composition according to the present invention may optionally further comprise a binder and a solvent incorporated therein. Examples of the solvent include esters such as butyl acetate, ethyl lactate and cellosolve acetate, ketones such as methyl ethyl ketone, cyclohexanone and methyl isobutyl ketone, halogenated hydrocarbons such as dichloromethane, 1,2-dichloroethane and chloroform, amides such as N,N-dimethylformamide, sulfoxides such as dimethyl sulfoxide, sulfolanes such as sulofolane, hydrocarbons such as cyclohexane and toluene, ethers such as tetrahydrofurane, ethyl ether and dioxane, alcohols such as ethanol, n-propanol, isopropanol and n-butanol diacetone alcohol, fluorine-based solvents such as 2,2,3,3-tetrafluoropropanol, and glycol ethers such as ethylene glycol monomethyl ether, ethylene glycol monoethyl ether and propylene glycol monomethyl ether. The aforementioned solvents may be used singly or in combination of two or more thereof taking into account the solubility of the compound used. The composition according to the present invention may further comprise various additives such as polymerization initiator, oxidation inhibitor, UV absorber, plasticizer and lubricant incorporated therein depending on the purpose.

Examples of the polymer binder employable herein include natural organic polymer material such as gelatin, cellulose derivative, dextran, rosin and rubber, and synthetic organic polymer material such as hydrocarbon-based resin (e.g., polyethylene, polypropylene, polystyrene, polyisobutyrene), vinyl-based resin (e.g., polyvinyl chloride, polyvinylidene chloride, polyvinyl chloride-polyvinyl acetate), acrylic resin (e.g., methyl polyacrylate, methyl polymethacrylate), and initial condensate of thermosetting resin (e.g., polyvinyl alcohol, chlorinatedpolyethylene, epoxy resin, butyral resin, rubber derivative, phenol-fomaldehyde resin).

The composition according to the present invention may be liquid or solid depending on the purpose.

The two-photon polymerization process according to the present invention will be described hereinafter. As the laser beam source to be used herein there may be used a laser beam having a wavelength longer than the linear absorption band of the compound of the general formula (1) and free of linear absorption. In some detail, a solid laser having an oscillation wavelength close to central wavelength of 1,000 nm, a semiconductor laser or solid laser having an oscillation wavelength close to 780 nm, a semiconductor laser or solid laser having an oscillation wavelength of from 620 nm to 680 nm, etc. may be used.

Embodiments of the optical data recording medium and recording process according to the present invention will be described hereinafter.

The optical data recording medium of the present invention comprises the compound represented by the general formula (1) incorporated therein.

Specific examples of synthesis of the compound represented by the general formula (1) are as described above.

The structure of the optical data recording medium of the present invention will be described hereinafter. The optical data recording medium of the present invention is not specifically limited so far as it has a compound represented by the general formula (1) incorporated therein. The optical data recording medium of the present invention may be formed by forming a recording layer containing a compound represented by the general formula (1) on a substrate to a small thickness or may be a block form having a compound represented by the general formula (1) dispersed in a polymer matrix.

In the case of the recording medium having a recording layer containing a compound represented by the general formula (1) formed on a substrate to a small thickness, the recording layer containing a compound represented by the general formula (1) is preferably provided on a transparent disk-shaped substrate having a thickness of from 0.1 mm to 3 mm having a pregroove (track pitch: from 0.1 to 2.0 µm) formed thereon. The pregroove may or may not be present.

The substrate (including a protective substrate) may be arbitrarily selected from various materials which have heretofore been used as substrate for optical data recording medium. Examples of these substrate materials include glass, polycarbonate, acrylic resin such as polymethyl methacrylate, vinyl chloride resin such as polyvinyl chloride and vinyl chloride copolymer, epoxy resin, amorphous polyolefin, and polyester. These substrate materials may be used in combination. These materials may be used in the form of film or rigid substrate. Preferred among these materials is polycarbonate from the standpoint of moisture resistance, dimensional stability and cost.

The pregroove, if provided on the substrate (or undercoating layer), is a tracking groove or a roughness (pregroove) for giving data such as address signal and is preferably formed directly on a substrate at the aforementioned track pitch during injection molding or extrusion molding of a resin material such as polycarbonate. Alternatively, the pregroove may be formed by providing a pregroove layer. As the material of the pregroove layer there may be used a mixture of at least one monomer (or oligomer) selected from the group consisting of acrylic acid monoester, diester, triester and tetraeter and a photopolymerization initiator. In order to form the pregroove layer, a mixture of the acrylic acid ester and polymerization initiator is applied to a precision-worked mold (stamper). A substrate is then put on the coated layer. The laminate is then irradiated with ultraviolet rays through the substrate and the mold so that the coat layer is hardened to fix the substrate to the coated layer. Subsequently, the substrate is released from the mold to obtain the pregroove layer. The thickness of the pregroove layer is from 0.05 µm to 100 µm, preferably from 0.1 µm to 50 µm.

A recording layer containing a dye compound of the present invention represented by the aforementioned general formula is then provided on the substrate (or undercoating layer) or the surface thereof on which the pregroove is formed. As a method for forming the recording layer there may be used a vacuum evaporation method or coating method. Examples of the coating method include spray coating method, spin coating method, dip coating method, roll coating method, blade coating method, doctor roll coating method, and screen printing method. The recording layer may be either a single layer or a multi-layer. The thickness of the recording layer may be normally in the range of from 20 µm to 1,000 µm, preferably from 50 µm to 500 µm. Further, by controlling the focal length of laser beam, multi-layer recording is made possible. In this case, a thicker recording layer can be provided, making it possible to effect higher density recording.

The formation of the recording layer by coating method can be carried out by dissolving a compound according to the present invention and optionally a binder in a solvent to prepare a coating solution, applying the coating solution to the surface of a substrate, and then drying the coat layer. Examples of the solvent for forming the dye recording layer include ester such as butyl acetate, ethyl lactate and cellosolve acetate, ketone such as methyl ethyl ketone, cyclohexanone and methyl isobutyl ketone, chlorinated hydrocarbon such as dichloromethane, 1,2-dichloroethane and chloroform, amide such as dimethylformamide, hydrocarbon such as cyclohexane, ether such a tetrahydrofurane, ethyl ether and dioxane, alcohol such as ethanol, n-propanol, isopropanol, n-butanol and diacetone alcohol, fluorine-based solvent such as 2,2,3, 3-tetrafluoropropanol, and glycol ether such as ethylene glycol monomethyl ether, ethylene glycol monoethyl ether and propylene glycol monomethyl ether. These solvents may be used singly or in combination of two or more thereof taking into account the solubility of the compound used. The coating solution may further comprise various additives such as oxidation inhibitor, UV absorbing material, plasticizer and lubricant incorporated therein according to the purpose.

Examples of the binder employable herein include natural organic polymer material such as gelatin, cellulose derivative, dextran, rosin and rubber, and synthetic organic polymer material such as hydrocarbon-based resin (e.g., polyethylene, polypropylene, polystyrene, polyisobutyrene), vinyl-based resin (e.g., polyvinyl chloride, polyvinylidene chloride, polyvinyl chloride-polyvinyl acetate), acrylic resin (e.g., methyl polyacrylate, methyl polymethacrylate), and initial condensate of thermosetting resin (e.g., polyvinyl alcohol, chlorinated polyethylene, epoxy resin, butyral resin, rubber derivative, phenol-fomaldehyde resin). In the case where such a binder, too, is used as a recording layer material, the amount of the binder to be used is normally from 0.01 to 50 times (by mass), preferably from 0.1 to 5 times (by mass (i.e., by weight)) that of the dye. The concentration of the dye in the coating solution thus prepared is normally in the range of from 0.01% to 10% by weight (i.e., by mass), preferably from 0.1% to 5% by weight.

The recording layer may comprise various discoloration inhibitors incorporated therein to enhance the light-resistance thereof. Examples of these discoloration inhibitors include organic oxidizing agents, and single state oxygen quenchers.

The substrate may have an undercoating layer provided on the recording layer side thereof for the purpose of improving the flatness thereof, enhancing the adhesion thereof and inhibiting the denaturation of the recording layer. Examples of the undercoating layer material include polymer materials such as polymethylmethacrylate, acrylic acid-methacrylic acid copolymer, styrene-maleic anhydride copolymer, polyvinyl alcohol, N-methylyolacrylamide, styrene-vinyl toluene copolymer, chlorosulfonated polyethylene, nitrocellulose, polyvinyl chloride, chlorinated polyolefin, polyester, polyimide, vinyl acetate-vinyl chloride copolymer, ethylene-vinyl acetate copolymer, polyethylene, polypropylene and polycarbonate, and surface modifiers such as silane coupling agent.

The recording layer may have a light reflecting layer provided thereon for the purpose of enhancing the reflectance during the reproduction of data. As the light-reflecting material to be used as a light reflecting layer material there may be used a material having a high reflectance with respect to laser beam. Examples of such a light-reflecting material include metal such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn and Bi, semimetal, and stainless steel. Preferred among these materials are Cr, Ni, Pt, Cu, Ag, Au, Al, and stainless steel. Particularly preferred among these materials is Ag. These materials may be used singly or in combination of two or more thereof. The light reflecting layer may be formed on the recording layer by vapor-depositing, sputtering or ion plating these light-reflecting materials. The thickness of the light reflecting layer is normally from 10 nm to 300 nm, preferably from 50 nm to 200 nm.

The light reflecting layer may have a protective layer provided thereon for the purpose of physically and chemically protecting the recording layer, etc. This protective layer may be provided also on the surface of the substrate opposite the recording layer for the purpose of enhancing the scratch resistance and moisture resistance of the substrate. Examples of the material to be used as the protective layer include inorganic materials such as SiO, $SiO_2$, $MgF_2$, $SnO_2$ and $Si_3N_4$, and organic materials such as thermoplastic resin, thermosetting resin and UV-curing resin. The protective layer can be formed, e.g., by laminating a film obtained by extruding a plastic onto a light-reflecting layer and/or substrate. Alternatively, vacuum evaporation, sputtering, coating or the like may be employed. The thermoplastic resin or thermosetting resin, if used, may be dissolved in a proper solvent to prepare a coating solution which is then applied and dried to form the protective layer. The UV-curing resin, if used, may be irradiated with ultraviolet rays as it is or in the form of coated layer obtained by the coating of a solution of the resin in a proper solvent. The coating solution may further comprise various additives such as antistatic agent, oxidation inhibitor and UV absorber incorporated therein according to the purpose. The thickness of the protective layer may be normally in the range of from 0.1 μm to 100 μm.

In the case where the optical data recording medium of the present invention is a block form having a compound represented by the general formula (1) dispersed in a polymer matrix, the polymer matrix in which the compound of the general formula (1) is to be dispersed is not specifically limited. Examples of the polymer matrix employable herein include acrylic resin such as polycarbonate and polymethyl methacrylate, epoxy resin, amorphous polyolefin, polyester, vinyl chloride-based resin, and polyethylene terephthalate.

It is necessary that the compound of the general formula (1) be incorporated in the polymer matrix in a proportion of from 1% to 90% by mass (i.e., by weight), preferably from 5% to 80% by mass. The block is preferably in the form of cube or rectangular parallelopiped having a length, a width and a height of from 1 mm to 100 mm each.

The process for dispersing the compound of the general formula (1) in the polymer matrix is not specifically limited. Various processes may be employed. Examples of the process for dispersing the compound of the general formula (1) in the polymer matrix include a process which comprises dissolving the polymer compound, adding the compound of the general formula (1) to the polymer compound, mixing the mixture uniformly, and then allowing the mixture to cool, a process which comprises dissolving the polymer compound and the compound of the general formula (1) in a proper solvent, and then heating the solution so that the solvent is evaporated, and a process which comprises dissolving the compound of the general formula (1) in a corresponding monomer, and then subjecting the solution to polymerization reaction so that it is polymerized.

The data recording process of the present invention will be described hereinafter. As the recording light source there may be used a laser beam having a wavelength longer than the linear absorption band of the compound of the general formula (1) and free of linear absorption. In some detail, a solid laser having an oscillation wavelength close to central wavelength of 1,000 nm, a semiconductor laser or solid laser having an oscillation wavelength close to 780 nm, a semiconductor laser or solid laser having an oscillation wavelength of from 620 nm to 680 nm, etc. may be used. The optical data recording medium of the present invention is irradiated with a recording laser beam such as semiconductor laser beam on the substrate side thereof while being rotated at a constant linear speed or constant angular velocity. When thus irradiated with laser beam, the recording layer has data recorded thereon. As previously described, the probability of two-photon absorption is proportional to the square of the intensity of laser with which the recording layer is irradiated. Thus, a pit having a smaller size than the spot size of laser beam inducing two-photon absorption is formed.

The two-photon absorption compound of the present invention and the light emitting process thereby will be further described hereinafter.

The two-photon absorption compound of the present invention is a compound represented by the general formula (1).

Specific examples of synthesis of the compound represented by the general formula (1) are as described above.

The process for emitting light according to the present invention comprises irradiating a compound represented by the general formula (1) with a laser beam having a wavelength longer than the linear absorption band of the compound represented by the general formula (1) to induce two-photon absorption, thereby emitting light.

EXAMPLE

The present invention will be further described in the following examples, but the present invention should not be construed as being limited thereto.

Example I-1

Example of Two-Photon Polymerization with 1,053 nm Laser Beam

Composition of Polymerizable Solution

Two-photon absorbing material 0.1 parts by weight (Table I-1)
Ultraviolet-curing resin (SCR-701, 100 parts by weight produced by D-MEC LTD.)

Comparative Example

Composition of Polymerizable Solution

An ultraviolet-curing resin SCR-701 (produced by D-MEC LTD.) was used free of two-photon absorbing material.

Evaluation of Properties:

A laser beam having a wavelength of 1,053 nm, an average power of 250 mW, a peak power of 1 kW, a pulse width of 3 ps and a repetition frequency of 82 Hz was passed through a lens (f=300 mm) so that it was condensed to a beam having a diameter of about 100 μm with which the polymerizable solution was then irradiated. The polymerizable solution was then visually judged for hardening. The results are set forth in Table I-1 below.

TABLE I-1

| Two-photon absorbing material | Presence or absence of hardening | Remarks |
|---|---|---|
| None | No | Comparative |
| (1) | Yes | Inventive |

TABLE I-1-continued

| Two-photon absorbing material | Presence or absence of hardening | Remarks |
|---|---|---|
| (9) | Yes | Inventive |
| (16) | Yes | Inventive |
| (31) | Yes | Inventive |

Example I-2

Example of Two-Photon Polymerization with 780 nm Laser Beam

| Composition of polymerizable solution | |
|---|---|
| Two-photon absorbing material (Table I-2) | 0.1 part by weight |
| Ultraviolet-curing resin (SCR-701, produced by D-MEC LTD.) | 100 parts by weight |

Evaluation of Properties:

A laser beam having a wavelength of 780 nm, an average power of 40 mW, a peak power of 7 kW, a pulse width of 100 fs and a repetition frequency of 48 Hz was passed through a lens (f-300 mm) so that it was condensed to a beam having a diameter of about 100 μm with which the polymerizable solution was then irradiated. The polymerizable solution was then visually judged for hardening. The results are set forth in Table I-2 below.

TABLE I-2

| Two-photon absorbing material | Presence or absence of hardening | Remarks |
|---|---|---|
| None | No | Comparative |
| (16) | Yes | Inventive |
| (18) | Yes | Inventive |
| (22) | Yes | Inventive |
| (89) | Yes | Inventive |

As is apparent from the foregoing results of evaluation, a two-photon polymerizable composition can be provided which can be polymerized with laser beams having various wavelengths and thus exhibits a good two-photon polymerization efficiency.

Example II-1

Preparation of Data Recording Medium 1 g of Compound (1) was dissolved in 100 ml of 1,2-dichloroethane to obtain a recording layer-forming coating solution. The coating solution thus obtained was then applied to a glass substrate by a spin coating method to prepare a data recording medium comprising a recording layer formed thereon.

Example II-2

Preparation of Data Recording Medium

A recording medium was prepared in the same manner as in Example II-1 except that Compound (9) was used instead of Compound (1).

Example II-3

Preparation of Data Recording Medium

A recording medium was prepared in the same manner as in Example II-1 except that Compound (16) was used instead of Compound (1) and 2,2,3,3-tetrafluoropropanol was used instead of 1,2-dichloroethane.

Example II-4

Preparation of Data Recording Medium

A recording medium was prepared in the same manner as in Example II-1 except that Compound (2) was used instead of Compound (1) and 2,2,3,3-tetrafluoropropanol was used instead of 1,2-dichloroethane.

Example II-5

Preparation of Data Recording Medium

A recording medium was prepared in the same manner as in Example II-1 except that Compound (4) was used instead of Compound (1).

Example II-6

Preparation of Data Recording Medium

A recording medium was prepared in the same manner as in Example II-1 except that Compound (6) was used instead of Compound (1) and 2,2,3,3-tetrafluoropropanol was used instead of 1,2-dichloroethane.

Example II-7

Preparation of Data Recording Medium

A recording medium was prepared in the same manner as in Example II-1 except that Compound (18) was used instead of Compound (1) and 2,2,3,3-tetrafluoropropanol was used instead of 1,2-dichloroethane.

Evaluation (1) of data recording medium: Recording at 1.06 μm

The data recording media prepared in Examples II-1, II-2 and II-3 were each irradiated with a 1.06 μm laser beam pulse having a peak power of 500 kW, a pulse with of 8 ns and a repetition frequency of 20 Hz. As a result, all these media were confirmed by AFM to have a good recording mark having a size of about 0.76 μm formed thereon.

Evaluation (2) of Data Recording Medium: Recording at 780 nm

The data recording media prepared in Examples II-4, II-5, II-6 and II-7 were each irradiated with a 790 nm laser beam pulse having a peak power of 5 kW, a pulse with of 100 fs and a repetition frequency of 50 Hz. As a result, all these media were confirmed by AFM to have a good recording mark having a size of about 680 nm formed thereon.

An optical data recording medium comprising a compound represented by the general formula (1) can provide a high density data recording medium.

The compound of the present invention was dissolved in chloroform. The emission spectrum obtained when the solution was irradiated with a 1,064 nm laser pulse from an Nd:YAG laser was then measured. From the area of the emission spectrum thus obtained was then determined non-resonant two-photon absorption induced emission intensity.

Example III

[Method for Evaluating Two-Photon Absorption Cross-Section]

The evaluation of two-photon absorption cross-section of the compound of the invention was carried out according to the method described in M. A. Albotu et al., "Appli. Opt.", 1998, 37, 7352. As a light source for the measurement of two-photon absorption cross-section there was used a Ti:sapphire pulse laser (pulse width: 100 fs; repetition frequency: 80 MHz; mean output: 1 W; peak power: 100 kW). The two-photon absorption cross-section was then measured at a wavelength of from 700 nm to 1,000 nm. As reference materials there were used rhodamine B and fluorescien. By correcting the resulting measurements by the value of two-photon absorption cross-section of rhodamine B and fluorescein described in C. Xu. et al., "J. Opt. Soc. Am. B", 1996, 18, 481, the two-photon absorption cross-section of the various compounds were determined. The sample to be measured for two-photon absorption was in the form of solution of compound having a concentration of from $1 \times 10^{-2}$ to $1 \times 10^{-4}$ M.

Example III-1

The compounds of the invention were each measured for two-photon absorption cross-section in the aforementioned manner. The results are set forth in Table III-1 with GM as a unit (1 GM=$1 \times 10^{-50}$ cm$^4$s/photon). The values set forth in Table III-1 represent the maximum value of two-photon absorption cross-section within the measuring wavelength range.

Comparative Example Iii-1

The two-photon absorption cross section of Comparative Compounds 1 and 2 having the following structures were measured in the aforementioned manner. The results are set forth in Table III-1.

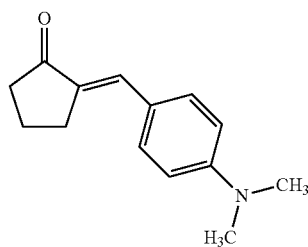

Comparative Compound 1

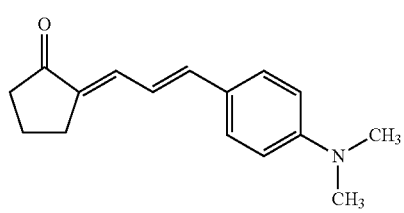

Comparative Compound 2

TABLE III-1

| Compound No. | Two-photon absorption cross section/GM |
|---|---|
| 1 | 970 |
| 2 | 224 |
| 3 | 1,970 |
| 8 | 192 |
| 9 | 1,300 |
| 15 | 813 |
| 29 | 843 |
| 71 | 648 |
| 72 | 177 |
| 73 | 340 |
| 100 | 900 |
| A01 | 1,210 |
| A02 | 500 |
| A03 | 1,460 |
| A04 | 1,140 |
| A05 | 722 |
| A06 | 2,070 |
| A07 | 2,290 |
| A17 | 2,510 |
| Comparative Compound 1 | 60 |
| Comparative Compound 2 | 145 |

[Method for Evaluating Two-Photon Absorption Induced Emission Intensity]

The compound of the invention was dissolved in chloroform. The emission spectrum obtained when the solution was irradiated with a 1,064 nm laser pulse from an Nd:YAG laser was then measured. From the area of the emission spectrum thus obtained was then determined non-resonance two-photon absorption induced emission intensity.

Example III-2

Sample 1:
0.40 g of the aforementioned compound (1) according to the present invention was dissolved in 100 ml of chloroform to prepare a $1 \times 10^{-2}$ M solution.
Sample 2:
0.41 g of the aforementioned compound (29) according to the present invention was dissolved in 100 ml of chloroform to prepare a $1 \times 10^{-2}$ M solution.
Comparative Sample 1:
0.59 g of a compound described in WO9709043 pamphlet as a compound emitting a strong two-photon light beam was dissolved in 100 ml of acetonitrile to prepare a $1 \times 10^{-2}$ M solution.
Comparative Compound: "Dye 1" Described in WO9709043

Samples 1 and 2 and Comparative Sample 1 were each irradiated with a 1,064 nm laser pulse from an Nd:YAG laser under the same conditions. The resulting non-resonant two-photon absorption induced emission spectrum was measured. The area of the emission spectrum (non-resonant two-photon absorption induced emission intensity) thus obtained is set forth in Table III-2 below relative to that of Comparative Sample 1 as 1.

TABLE III-2

| Sample | Compound | Non-resonant two-photon emission intensity |
|---|---|---|
| Sample 1 | Compound (1) | 20 |
| Sample 2 | Compound (29) | 8.8 |
| Comparative Sample 1 | "Dye 1" described in WO9709043 | 1 |

As is apparent from the results of Table III-2, the inventive samples exhibit far better properties than the conventional materials.

Example III-3

Sample 3:
0.37 g of the aforementioned compound (15) according to the present invention was dissolved in 100 ml of chloroform to prepare a $1 \times 10^{-2}$ M solution.
Comparative Sample 2:
0.59 g of ASPT as used in Comparative Sample 1 was dissolved in 100 ml of THF to prepare a $1 \times 10^{-2}$ M solution.

Samples 1, 2 and 3 and Comparative Sample 2 obtained in Example III-1 were each irradiated with a 1,064 nm laser pulse from an Nd:YAG laser. The resulting non-resonant two-photon absorption induced emission spectrum was measured. The area of the emission spectrum thus obtained is set forth in Table III-2 below relative to that of Comparative Sample 2 as 1.

TABLE III-3

| Sample | Compound | Non-resonant two-photon emission intensity |
|---|---|---|
| Sample 1 | Compound (1) | 3.9 |
| Sample 2 | Compound (29) | 1.7 |
| Sample 3 | Compound (15) | 2.9 |
| Comparative Sample 2 | "Dye 1" described in WO9709043 | 1 |

As is apparent from the results of Table III-3, the inventive samples exhibit far better properties than the conventional materials.

The use of the compound of the present invention makes it possible to obtain a non-resonant two-photon absorption induced light-emitting material which exhibits a far stronger non-resonant two-photon absorption induced emission intensity than ever.

The entitle disclosure of each and every foreign patent application from which the benefit of foreign priority has been claimed in the present application is incorporated herein by reference, as if fully set forth herein.

While the present invention has been described in detail and with reference to specific embodiments thereof, it will be apparent to one skilled in the art that various changes and modifications can be made therein without departing from the spirit and scope thereof.

What is claimed is:

1. A non-resonance two-photon absorption induction method which comprises irradiating a compound represented by the general formula (1) with laser beam having a wavelength longer than the linear absorption band of the compound of the general formula (1) to induce non-resonance two-photon absorption:

$$X^2-(-CR^4=CR^3-)_m-C(=O)-(-CR^1=CR^2-)_n-X^1 \quad (1)$$

wherein X$^1$ and X$^2$ may be the same or different, each represent a substituted or unsubstituted aryl or a substituted or unsubstituted heterocyclic; R$^1$, R$^2$, R$^3$ and R$^4$ each independently represent a hydrogen atom or some of R$^1$, R$^2$, R$^3$ and R$^4$ may be connected to each other to form at least one 5-, 6- or 7-membered ring; and n and m, each independently represent an integer of from 1 to 4, with the proviso that when n or m is 2 or more, the plurality of R$^1$'s, R$^2$'s, R$^3$'s, and R$^4$'s each may be the same or different, wherein the substituted aryl for X$^1$ and X$^2$ is an aryl substituted with at least one selected from the group consisting of a C$_1$-C$_{20}$ linear or cyclic alkyl, a C$_6$-C$_{18}$ unsubstituted aryl, a C$_2$-C$_{20}$ alkenyl, a C$_2$-C$_{20}$ alkynyl, a halogen atom, a C$_2$-C$_{20}$ amino, a cyano, a hydroxyl, a carboxyl, a C$_2$-C$_{10}$ acyl, a C$_1$-C$_{20}$ alkoxy, a C$_6$-C$_{18}$ aryloxy, a C$_1$-C$_{20}$ alkylthio, a C$_6$-C$_{18}$ arylthio, a C$_1$-C$_{20}$ alkylsulfonyl, a C$_6$-C$_{18}$ arylsulfonyl, a C$_1$-C$_{10}$ carbamoyl, a C$_1$-C$_{10}$ amide, a C$_2$-C$_{12}$ imide, a C$_2$-C$_{10}$ acyloxy, a C$_2$-C$_{10}$ alkoxycarbonyl, and a C$_1$-C$_{10}$ heterocyclic, and the substituted heterocyclic for X$^1$ and X$^2$ is a heterocyclic substituted with at least one selected from the group consisting of a C$_1$-C$_{20}$ linear or cyclic alkyl, a C$_6$-C$_{18}$ unsubstituted aryl, a C$_2$-C$_{20}$ alkenyl, a C$_2$-C$_{20}$ alkynyl, a halogen atom, a C$_2$-C$_{20}$ amino, a cyano, a hydroxyl, a carboxyl, a C$_2$-C$_{10}$ acyl, a C$_1$-C$_{20}$ alkoxy, a C$_6$-C$_{18}$ aryloxy, a C$_1$-C$_{20}$ alkylthio, a C$_6$-C$_{18}$ arylthio, a C$_1$-C$_{20}$ alkylsulfonyl, a C$_6$-C$_{18}$ arylsulfonyl, a C$_1$-C$_{10}$ carbamoyl, a C$_1$-C$_{10}$ amide, a C$_2$-C$_{12}$ imide, a C$_2$-C$_{10}$ acyloxy, a C$_2$-C$_{10}$ alkoxycarbonyl, and a C$_1$-C$_{10}$ heterocyclic.

2. The non-resonance two-photon absorption induction method according to claim 1, wherein a cyclic structure formed by R$^1$, R$^2$, R$^3$ and R$^4$ is a 5- or 6-membered ring.

3. The non-resonance two-photon absorption induction method according to claim 1, wherein X$^1$ and X$^2$ may be the same or different, each represent a C$_6$-C$_{30}$ substituted or unsubstituted aryl or a C$_1$-C$_{10}$ substituted or unsubstituted heterocyclic.

4. The non-resonance two-photon absorption induction method according to claim 1, wherein the compound represented by the general formula (1) is:

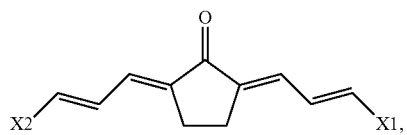

wherein both X$^1$ and X$^2$ are represented by:

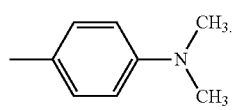

5. A light emitting method which comprises irradiating a compound represented by the general formula (1) with laser beam having a wavelength longer than the linear absorption band of the compound of the general formula (1) to induce non-resonance two-photon absorption, thereby causing light emission:

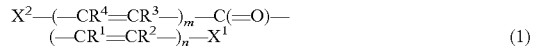

wherein X$^1$ and X$^2$ may be the same or different, each represent a substituted or unsubstituted aryl or substituted or unsubstituted heterocyclic; R$^1$, R$^2$, R$^3$ and R$^4$ each independently represent a hydrogen atom or some of R$^1$, R$^2$, R$^3$ and R$^4$ may be connected to each other to form a 5-, 6- or 7-membered ring; and n and m, each independently represent an integer of from 1 to 4, with the proviso that when norm is 2 or more, the plurality of R$^1$'s, R$^2$'s, R$^3$'s, and R$^4$'s each may be the same or different, wherein the substituted aryl for X$^1$ and X$^2$ is an aryl substituted with at least one selected from the group consisting of a C$_1$-C$_{20}$ linear or cyclic alkyl, a C$_6$-C$_{18}$ unsubstituted aryl, a C$_2$-C$_{20}$ alkenyl, a C$_2$-C$_{20}$ alkynyl, a halogen atom, a C$_2$-C$_{20}$ amino, a cyano, a hydroxyl, a carboxyl, a C$_2$-C$_{10}$ acyl, a C$_1$-C$_{20}$ alkoxy, a C$_6$-C$_{18}$ aryloxy, a C$_1$-C$_{20}$ alkylthio, a C$_6$-C$_{18}$ arylthio, a C$_1$-C$_{20}$ alkylsulfonyl, a C$_6$-C$_{18}$ arylsulfonyl, a C$_1$-C$_{10}$ carbamoyl, a C$_1$-C$_{10}$ amide, a C$_2$-C$_{12}$ imide, a C$_2$-C$_{10}$ acyloxy, a C$_2$-C$_{10}$ alkoxycarbonyl, and a C$_1$-C$_{10}$ heterocyclic, and the substituted heterocyclic for X$^1$ and X$^2$ is a heterocyclic substituted with at least one selected from the group consisting of a C$_1$-C$_{20}$ linear or cyclic alkyl, a C$_6$-C$_{18}$ unsubstituted aryl, a C$_2$-C$_{20}$ alkenyl, a C$_2$-C$_{20}$ alkynyl, a halogen atom, a C$_2$-C$_{20}$ amino, a cyano, a hydroxyl, a carboxyl, a C$_2$-C$_{10}$ acyl, a C$_1$-C$_{20}$ alkoxy, a C$_6$-C$_{18}$ aryloxy, a C$_1$-C$_{20}$ alkylthio, a C$_6$-C$_{18}$ arylthio, a C$_1$-C$_{20}$ alkylsulfonyl, a C$_6$-C$_{18}$ arylsulfonyl, a C$_1$-C$_{10}$ carbamoyl, a C$_1$-C$_{10}$ amide, a C$_2$-C$_{12}$ imide, a C$_2$-C$_{10}$ acyloxy, a C$_2$-C$_{10}$ alkoxycarbonyl, and a C$_1$-C$_{10}$ heterocyclic.

6. The light emitting method according to claim 5, wherein a cyclic structure formed by R$^1$, R$^2$, R$^3$ and R$^4$ is a 5- or 6-membered ring.

7. The light emitting method according to claim 5, wherein X$^1$ and X$^2$ may be the same or different, each represent a C$_6$-C$_{30}$ substituted or unsubstituted aryl or a C$_1$-C$_{10}$ substituted or unsubstituted heterocyclic.

8. The light emitting method according to claim 5, wherein the compound represented by the general formula (1) is:

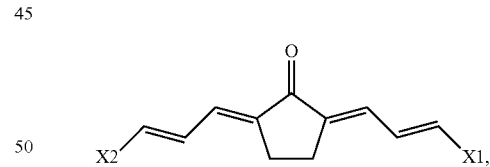

wherein both X$^1$ and X$^2$ are represented by:

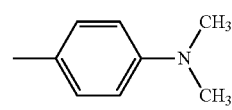

* * * * *